United States Patent
Cho et al.

(10) Patent No.: US 12,232,851 B2
(45) Date of Patent: Feb. 25, 2025

(54) ACUTE HEALTH EVENT MONITORING

(71) Applicant: Medtronic, Inc., Minneapolis, MN (US)

(72) Inventors: Yong K. Cho, Excelsior, MN (US); Ryan D. Wyszynski, Oak Grove, MN (US); Grant A. Neitzell, Plymouth, MN (US); Paul G. Krause, Mahtomedi, MN (US); Kevin T. Ousdigian, Shoreview, MN (US); Paul J. DeGroot, Minneapolis, MN (US); Shantanu Sarkar, Roseville, MN (US); Christopher D. Koch, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 17/246,331

(22) Filed: Apr. 30, 2021

(65) Prior Publication Data

US 2022/0369937 A1 Nov. 24, 2022

Related U.S. Application Data

(60) Provisional application No. 63/158,189, filed on Mar. 8, 2021.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0031* (2013.01); *A61B 5/0059* (2013.01);
(Continued)

(58) Field of Classification Search
CPC ......... A61B 5/053; A61B 5/0059; A61B 7/00; A61B 5/7275; A61B 5/7264;
(Continued)

(56) References Cited

U.S. PATENT DOCUMENTS

| 3,552,386 A | 1/1971 | Horth |
| 3,598,110 A | 8/1971 | Edmark |

(Continued)

FOREIGN PATENT DOCUMENTS

| CA | 3075015 A1 | 9/2021 |
| CN | 105068486 A | 11/2015 |

(Continued)

OTHER PUBLICATIONS

Samani et al., "Robotic Automated External Defibrillator Ambulance for Emergency Medical Service in Smart Cities," IEEE Access, vol. 4., Jan. 2016, pp. 268-283.

(Continued)

*Primary Examiner* — Lynsey C Eiseman
*Assistant Examiner* — Amanda L Steinberg
(74) *Attorney, Agent, or Firm* — Shumaker & Sieffert, P.A.

(57) ABSTRACT

A system comprises processing circuitry and memory comprising program instructions that, when executed by the processing circuitry, cause the processing circuitry to: apply a first set of rules to first patient parameter data for a first determination of whether sudden cardiac arrest of a patient is detected; determine that a one or more context criteria of the first determination are satisfied; and in response to satisfaction of the context criteria, apply a second set of rules to second patient parameter data for a second determination of whether sudden cardiac arrest of the patient is detected. At least the second set of rules comprises a machine learning model, and the second patient parameter data comprises at (Continued)

least one patient parameter that is not included in the first patient parameter data.

23 Claims, 8 Drawing Sheets

(51) Int. Cl.
*A61B 5/021* (2006.01)
*A61B 5/053* (2021.01)
*A61B 5/08* (2006.01)
*A61B 5/11* (2006.01)
*A61B 5/318* (2021.01)
*A61B 7/00* (2006.01)

(52) U.S. Cl.
CPC .............. *A61B 5/021* (2013.01); *A61B 5/053* (2013.01); *A61B 5/0816* (2013.01); *A61B 5/1116* (2013.01); *A61B 5/1118* (2013.01); *A61B 5/318* (2021.01); *A61B 5/686* (2013.01); *A61B 5/7221* (2013.01); *A61B 5/7264* (2013.01); *A61B 5/7275* (2013.01); *A61B 7/00* (2013.01)

(58) Field of Classification Search
CPC ... A61B 5/7221; A61B 5/1118; A61B 5/1116; A61B 5/686; A61B 5/021; A61B 5/0205; A61B 5/318
See application file for complete search history.

(56) References Cited

U.S. PATENT DOCUMENTS

| | | | |
|---|---|---|---|
| 3,658,055 A | 4/1972 | Abe et al. |
| 3,677,260 A | 7/1972 | Funfstuck et al. |
| 3,828,768 A | 8/1974 | Douglas |
| 3,861,387 A | 1/1975 | Lawhorn et al. |
| 3,927,663 A | 12/1975 | Russell et al. |
| 4,023,564 A | 5/1977 | Valiquette et al. |
| 4,306,567 A | 12/1981 | Krasner |
| 4,457,315 A | 6/1984 | Bennish |
| 4,958,641 A | 9/1990 | Digby et al. |
| 5,065,766 A | 11/1991 | Sasaki |
| 5,217,021 A | 6/1993 | Steinhaus et al. |
| 5,228,449 A | 7/1993 | Christ et al. |
| 5,271,411 A | 12/1993 | Ripley et al. |
| 5,366,487 A | 11/1994 | Adams et al. |
| 5,404,877 A | 4/1995 | Nolan et al. |
| 5,416,695 A | 5/1995 | Stutman et al. |
| 5,458,123 A | 10/1995 | Unger |
| 5,944,680 A | 8/1999 | Christopherson et al. |
| 6,095,984 A | 8/2000 | Amano et al. |
| 6,129,678 A | 10/2000 | Ryan et al. |
| 6,292,687 B1 | 9/2001 | Lowell et al. |
| 6,485,429 B2 | 11/2002 | Forstner |
| 6,487,442 B1 | 11/2002 | Wood |
| 6,490,478 B1 | 12/2002 | Zhang et al. |
| 6,493,581 B2 | 12/2002 | Russell |
| 6,609,023 B1 | 8/2003 | Fischell et al. |
| 6,907,238 B2 | 6/2005 | Leung |
| 6,980,112 B2 | 12/2005 | Nee |
| 7,076,290 B2 | 7/2006 | Sheth et al. |
| 7,092,751 B2 | 8/2006 | Erkkila |
| 7,117,031 B2 | 10/2006 | Lohman et al. |
| 7,194,354 B1 | 3/2007 | Oran et al. |
| 7,212,849 B2 | 5/2007 | Zhang et al. |
| 7,312,709 B2 | 12/2007 | Kingston |
| 7,343,199 B2 | 3/2008 | Hatlestad et al. |
| 7,353,179 B2 | 4/2008 | Ott et al. |
| 7,396,330 B2 | 7/2008 | Banet et al. |
| 7,480,529 B2 | 1/2009 | Li |
| 7,502,498 B2 | 3/2009 | Wen et al. |
| 7,558,623 B2 | 7/2009 | Fischell et al. |
| 7,689,282 B2 | 3/2010 | Zhang et al. |
| 7,702,382 B2 | 4/2010 | Xue |
| 7,715,905 B2 | 5/2010 | Kurzweil et al. |
| 7,733,224 B2 | 6/2010 | Tran |
| 7,801,596 B2 | 9/2010 | Fischell et al. |
| 7,840,277 B2 | 11/2010 | Matos |
| 7,844,323 B2 | 11/2010 | Fischell et al. |
| 7,846,106 B2 | 12/2010 | Andrews et al. |
| 7,860,559 B2 | 12/2010 | Fischell et al. |
| 7,889,092 B2 | 2/2011 | Volk et al. |
| 7,894,883 B2 | 2/2011 | Gunderson et al. |
| 7,991,460 B2 | 8/2011 | Fischell et al. |
| 8,002,701 B2 | 8/2011 | John et al. |
| 8,073,536 B2 | 12/2011 | Gunderson et al. |
| 8,073,537 B2 | 12/2011 | Gunderson et al. |
| 8,108,036 B2 | 1/2012 | Tran |
| 8,112,153 B2 | 2/2012 | Giftakis et al. |
| 8,170,609 B2 | 5/2012 | Hedtke et al. |
| 8,170,653 B2 | 5/2012 | Fischell et al. |
| 8,204,580 B2 | 6/2012 | Kurzweil et al. |
| 8,214,043 B2 | 7/2012 | Matos |
| 8,224,430 B2 | 7/2012 | Fischell et al. |
| 8,239,020 B2 | 8/2012 | Zhang et al. |
| 8,265,740 B2 | 9/2012 | Fischell et al. |
| 8,265,751 B2 | 9/2012 | Zhang et al. |
| 8,275,457 B1 * | 9/2012 | Fischell ................. A61B 5/349 607/9 |
| 8,301,236 B2 | 10/2012 | Baumann et al. |
| 8,332,233 B2 | 12/2012 | Ott et al. |
| 8,352,018 B2 | 1/2013 | Xue |
| 8,369,936 B2 | 2/2013 | Farringdon et al. |
| 8,401,644 B2 | 3/2013 | Gunderson et al. |
| 8,423,128 B2 | 4/2013 | Goto |
| 8,433,399 B1 | 4/2013 | Nosrati et al. |
| 8,437,840 B2 | 5/2013 | Patel et al. |
| 8,461,988 B2 | 6/2013 | Tran |
| 8,473,065 B2 | 6/2013 | Matos |
| 8,483,807 B2 | 7/2013 | Kurzweil et al. |
| 8,512,257 B2 | 8/2013 | Fischell et al. |
| 8,521,281 B2 | 8/2013 | Patel et al. |
| 8,525,673 B2 | 9/2013 | Tran |
| 8,525,687 B2 | 9/2013 | Tran |
| 8,531,291 B2 | 9/2013 | Tran |
| 8,554,315 B2 | 10/2013 | Cho et al. |
| 8,560,069 B2 | 10/2013 | Zhang |
| 8,562,524 B2 | 10/2013 | Osorio |
| 8,565,882 B2 | 10/2013 | Matos |
| 8,583,251 B2 | 11/2013 | Matos |
| 8,630,702 B2 | 1/2014 | Fischell et al. |
| 8,680,991 B2 | 3/2014 | Tran |
| 8,682,284 B2 | 3/2014 | Brackett et al. |
| 8,684,922 B2 | 4/2014 | Tran |
| 8,706,217 B2 | 4/2014 | Bardy et al. |
| 8,706,225 B2 | 4/2014 | Matos |
| 8,718,752 B2 | 5/2014 | Libbus et al. |
| 8,738,120 B2 | 5/2014 | Björling et al. |
| 8,747,336 B2 | 6/2014 | Tran |
| 8,774,908 B2 | 7/2014 | Stewart |
| 8,774,909 B2 | 7/2014 | Patel et al. |
| 8,805,529 B2 | 8/2014 | Matos |
| 8,825,146 B2 | 9/2014 | Li |
| 8,831,725 B2 | 9/2014 | Gunderson et al. |
| 8,849,400 B2 | 9/2014 | Gunderson et al. |
| 8,855,550 B2 | 10/2014 | Gaines et al. |
| 8,862,393 B2 | 10/2014 | Zhou et al. |
| 8,886,296 B2 | 11/2014 | Patel |
| 8,909,332 B2 | 12/2014 | Vitali et al. |
| 8,923,960 B2 | 12/2014 | Goto |
| 8,954,137 B2 | 2/2015 | Kurzweil et al. |
| 8,965,494 B2 | 2/2015 | Fischell et al. |
| 8,983,587 B2 | 3/2015 | Kurzweil et al. |
| 8,983,682 B1 | 3/2015 | Peeters et al. |
| 9,028,405 B2 | 5/2015 | Tran |
| 9,031,645 B2 | 5/2015 | Houben et al. |
| 9,044,148 B2 | 6/2015 | Michelson et al. |
| 9,060,746 B2 | 6/2015 | Weng et al. |
| 9,082,156 B2 | 7/2015 | Matos |
| 9,095,727 B2 | 8/2015 | Matos |
| 9,101,278 B2 | 8/2015 | Fischell et al. |
| 9,113,830 B2 | 8/2015 | Galen et al. |

(56) References Cited

U.S. PATENT DOCUMENTS

| | | |
|---|---|---|
| 9,138,590 B2 | 9/2015 | Zhang et al. |
| 9,179,255 B2 | 11/2015 | Stephens et al. |
| 9,179,851 B2 | 11/2015 | Baumann et al. |
| 9,204,796 B2 | 12/2015 | Tran |
| 9,237,243 B2 | 1/2016 | Jensen et al. |
| 9,241,677 B2 | 1/2016 | Liao-Chen et al. |
| 9,254,092 B2 | 2/2016 | Albert et al. |
| 9,293,025 B2 | 3/2016 | Zhang |
| 9,307,383 B1 | 4/2016 | Patrick |
| 9,314,181 B2 | 4/2016 | Brockway et al. |
| 9,351,640 B2 | 5/2016 | Tran |
| 9,364,158 B2 | 6/2016 | Banet et al. |
| 9,445,736 B2 | 9/2016 | Kurzweil et al. |
| 9,456,787 B2 | 10/2016 | Venkatraman et al. |
| 9,468,383 B2 | 10/2016 | Fischell et al. |
| 9,491,277 B2 | 11/2016 | Vincent |
| 9,498,152 B2 | 11/2016 | Bowers |
| 9,642,167 B1 | 5/2017 | Snyder et al. |
| 9,662,015 B2 | 5/2017 | Proud et al. |
| 9,668,665 B2 | 6/2017 | Schroeder et al. |
| 9,681,814 B2 | 6/2017 | Galloway et al. |
| 9,724,008 B2 | 8/2017 | Sullivan et al. |
| 9,724,046 B2 | 8/2017 | Forstner |
| 9,730,604 B2 | 8/2017 | Li et al. |
| 9,735,896 B2 | 8/2017 | Flippo et al. |
| 9,770,181 B2 | 9/2017 | Kurzweil et al. |
| 9,775,520 B2 | 10/2017 | Tran |
| 9,820,667 B2 | 11/2017 | Ting et al. |
| 9,824,188 B2 | 11/2017 | Brown et al. |
| 9,826,358 B2 | 11/2017 | Ryan et al. |
| 9,852,599 B1 | 12/2017 | Slavin et al. |
| 9,855,434 B2 | 1/2018 | Matos |
| 9,901,252 B2 | 2/2018 | Tran |
| 9,913,583 B2 | 3/2018 | Smith, Sr. |
| 9,979,810 B2 | 5/2018 | Mazar et al. |
| 9,997,055 B2 | 6/2018 | Ball |
| 10,003,394 B2 | 6/2018 | Bromberg et al. |
| 10,039,469 B2 | 8/2018 | Higgins et al. |
| 10,044,857 B2 | 8/2018 | Philbin |
| 10,085,115 B2 | 9/2018 | Mayor et al. |
| 10,098,561 B2 | 10/2018 | Brockway et al. |
| 10,117,595 B2 | 11/2018 | Chang et al. |
| 10,117,606 B2 | 11/2018 | Feldman et al. |
| 10,123,741 B2 | 11/2018 | Wang et al. |
| 10,136,826 B2 | 11/2018 | Sullivan et al. |
| 10,165,400 B2 | 12/2018 | Raj |
| 10,201,710 B2 | 2/2019 | Jackson et al. |
| 10,206,593 B2 | 2/2019 | Ukil et al. |
| 10,272,010 B2 | 4/2019 | Freeman et al. |
| 10,278,050 B2 | 4/2019 | Winkler et al. |
| 10,278,607 B2 | 5/2019 | Prystowsky et al. |
| 10,307,060 B2 | 6/2019 | Tran |
| 10,362,940 B2 | 7/2019 | Tran |
| 10,368,807 B2 | 8/2019 | Melker et al. |
| 10,375,558 B2 | 8/2019 | Katz et al. |
| 10,420,529 B2 | 9/2019 | Wang et al. |
| 10,463,295 B2 | 11/2019 | Zhou |
| 10,492,686 B2 | 12/2019 | Hunter et al. |
| 10,517,479 B2 | 12/2019 | Tran |
| 10,524,736 B2 | 1/2020 | Gross |
| 10,531,266 B2 | 1/2020 | Rauner et al. |
| 10,537,263 B2 | 1/2020 | Català |
| 10,540,878 B2 | 1/2020 | Hunter et al. |
| 10,575,748 B2 | 3/2020 | Higgins et al. |
| 10,595,731 B2 | 3/2020 | Gopalakrishnan et al. |
| 10,602,942 B2 | 3/2020 | Shakur et al. |
| 10,616,664 B2 | 4/2020 | Alman et al. |
| 10,616,747 B2 | 4/2020 | Piett et al. |
| 10,617,356 B2 | 4/2020 | Wang et al. |
| 10,624,550 B2 | 4/2020 | Soli et al. |
| 10,631,742 B2 | 4/2020 | Tal et al. |
| 10,657,796 B2 | 5/2020 | Bowers |
| 10,674,342 B2 | 6/2020 | Park et al. |
| 10,736,532 B2 | 8/2020 | Bardy et al. |
| 10,758,140 B2 | 9/2020 | Kurzweil et al. |
| 10,796,552 B2 | 10/2020 | Fahey |
| 10,814,978 B2 | 10/2020 | Walker et al. |
| 10,882,180 B2 | 1/2021 | Wright et al. |
| 10,888,705 B2 | 1/2021 | Matos |
| 10,905,328 B2 | 2/2021 | Murphy et al. |
| 10,981,009 B2 | 4/2021 | Jackson et al. |
| 11,024,432 B2 | 6/2021 | Chiu et al. |
| 11,064,339 B2 | 7/2021 | Hamre et al. |
| 11,103,176 B2 | 8/2021 | Galloway et al. |
| 11,103,194 B2 | 8/2021 | Galloway et al. |
| 11,116,989 B2 | 9/2021 | Gill et al. |
| 11,160,484 B2 | 11/2021 | Sullivan et al. |
| 11,197,629 B2 | 12/2021 | Remes et al. |
| 11,198,017 B2 | 12/2021 | Kaib et al. |
| 11,202,174 B2 | 12/2021 | Klinkner et al. |
| 11,218,584 B2 | 1/2022 | Martin et al. |
| 11,219,373 B2 | 1/2022 | Eggers et al. |
| 11,228,891 B2 | 1/2022 | King-Berkman et al. |
| 11,230,242 B2 | 1/2022 | Makled et al. |
| 11,234,604 B2 | 2/2022 | Albert |
| 11,278,201 B2 | 3/2022 | Thomson et al. |
| 11,289,197 B1 | 3/2022 | Park et al. |
| 11,291,401 B2 | 4/2022 | Velo |
| 11,311,230 B2 | 4/2022 | Sullivan et al. |
| 11,341,839 B2 | 5/2022 | Cruver et al. |
| 11,344,244 B2 | 5/2022 | Albert |
| 11,363,952 B2 | 6/2022 | Venkatraman et al. |
| 11,406,314 B2 | 8/2022 | Henry et al. |
| 11,623,102 B2 | 4/2023 | Schulhauser et al. |
| 11,633,112 B2 | 4/2023 | Stadler et al. |
| 11,679,268 B2 | 6/2023 | Haddad et al. |
| 2003/0023175 A1 | 1/2003 | Arzbaecher et al. |
| 2003/0176798 A1 | 9/2003 | Simon |
| 2003/0191402 A1 | 10/2003 | Arzbaecher et al. |
| 2003/0214409 A1 | 11/2003 | Hickle |
| 2003/0233129 A1 | 12/2003 | Matos |
| 2004/0172069 A1 | 9/2004 | Hakala |
| 2004/0199212 A1 | 10/2004 | Fischell et al. |
| 2005/0065445 A1 | 3/2005 | Arzbaecher et al. |
| 2005/0154325 A1 | 7/2005 | Lauter et al. |
| 2005/0228305 A1 | 10/2005 | Nagata et al. |
| 2006/0030781 A1 | 2/2006 | Shennib |
| 2006/0155206 A1* | 7/2006 | Lynn ................. A61B 5/4818 600/323 |
| 2006/0173498 A1 | 8/2006 | Banville et al. |
| 2006/0264767 A1 | 11/2006 | Shennib |
| 2006/0284732 A1 | 12/2006 | Brock-Fisher |
| 2007/0043585 A1 | 2/2007 | Matos |
| 2007/0249944 A1 | 10/2007 | Fischell et al. |
| 2007/0260285 A1* | 11/2007 | Libbus ............... A61N 1/36564 607/9 |
| 2007/0260289 A1 | 11/2007 | Giftakis et al. |
| 2007/0293775 A1 | 12/2007 | Fischell et al. |
| 2007/0299473 A1 | 12/2007 | Matos |
| 2008/0058660 A1 | 3/2008 | Fischell et al. |
| 2008/0064973 A1 | 3/2008 | Fischell et al. |
| 2008/0139954 A1 | 6/2008 | Day et al. |
| 2008/0177194 A1* | 7/2008 | Zhang ................. A61N 1/365 600/513 |
| 2008/0270036 A1 | 10/2008 | Webb |
| 2009/0054027 A1 | 2/2009 | Jenkins |
| 2009/0062670 A1 | 3/2009 | Sterling et al. |
| 2009/0076559 A1 | 3/2009 | Libbus et al. |
| 2009/0240156 A1 | 9/2009 | Fischell et al. |
| 2009/0322513 A1 | 12/2009 | Hwang et al. |
| 2009/0326595 A1 | 12/2009 | Brockway et al. |
| 2010/0016746 A1 | 1/2010 | Hampton et al. |
| 2010/0022902 A1 | 1/2010 | Lee et al. |
| 2011/0054934 A1 | 3/2011 | Vesto |
| 2011/0105928 A1 | 5/2011 | Bojovic et al. |
| 2011/0112417 A1 | 5/2011 | Gunderson et al. |
| 2011/0193704 A1 | 8/2011 | Harper et al. |
| 2011/0230161 A1 | 9/2011 | Newman |
| 2011/0288417 A1 | 11/2011 | Pinter et al. |
| 2012/0190969 A1 | 7/2012 | Kameli |
| 2012/0191150 A1 | 7/2012 | Kameli |
| 2012/0191151 A1 | 7/2012 | Kameli |
| 2012/0191152 A1 | 7/2012 | Kameli |
| 2012/0220835 A1 | 8/2012 | Chung |

(56) References Cited

U.S. PATENT DOCUMENTS

| | | |
|---|---|---|
| 2012/0242501 A1 | 9/2012 | Tran et al. |
| 2012/0306652 A1 | 12/2012 | Musiol et al. |
| 2012/0330171 A1 | 12/2012 | Zhang et al. |
| 2013/0095459 A1 | 4/2013 | Tran |
| 2013/0211291 A1 | 8/2013 | Tran |
| 2013/0245466 A1* | 9/2013 | Sachanandani .... A61N 1/37252 600/483 |
| 2014/0100497 A1 | 4/2014 | Hayashi et al. |
| 2014/0152436 A1 | 6/2014 | Langer |
| 2014/0163425 A1 | 6/2014 | Tran |
| 2014/0213202 A1 | 7/2014 | Wang et al. |
| 2014/0293053 A1 | 10/2014 | Chuang |
| 2015/0018658 A1 | 1/2015 | Fischell et al. |
| 2015/0112605 A1 | 4/2015 | Watson et al. |
| 2015/0118658 A1 | 4/2015 | Mayou et al. |
| 2015/0158988 A1 | 6/2015 | Sawaki et al. |
| 2015/0173689 A1 | 6/2015 | Owen et al. |
| 2015/0223759 A1* | 8/2015 | Ong .................. A61B 5/0205 600/301 |
| 2015/0302539 A1 | 10/2015 | Mazar et al. |
| 2015/0366518 A1* | 12/2015 | Sampson ............ A61B 5/0261 600/301 |
| 2016/0008614 A1 | 1/2016 | Zhang et al. |
| 2016/0035204 A1 | 2/2016 | Jansen |
| 2016/0106378 A1 | 4/2016 | Kyal et al. |
| 2016/0120434 A1* | 5/2016 | Park .................. A61B 5/4839 600/301 |
| 2016/0128595 A1 | 5/2016 | Fischell et al. |
| 2016/0135706 A1* | 5/2016 | Sullivan ............. A61B 5/1118 600/301 |
| 2016/0151021 A1 | 6/2016 | Feng et al. |
| 2016/0174857 A1 | 6/2016 | Eggers et al. |
| 2016/0174875 A1 | 6/2016 | Forster et al. |
| 2016/0325107 A1 | 11/2016 | Park et al. |
| 2016/0328950 A1 | 11/2016 | Pelletier et al. |
| 2016/0331330 A1 | 11/2016 | Freeman et al. |
| 2017/0007167 A1 | 1/2017 | Kostic et al. |
| 2017/0083667 A1 | 3/2017 | Darrah et al. |
| 2017/0246329 A1 | 8/2017 | Lloyd |
| 2017/0281097 A1* | 10/2017 | Thakur ............... A61N 1/36585 |
| 2017/0296076 A1 | 10/2017 | Mahajan et al. |
| 2017/0323485 A1 | 11/2017 | Samec et al. |
| 2017/0330438 A1 | 11/2017 | Howard et al. |
| 2017/0354365 A1* | 12/2017 | Zhou ................... A61N 1/395 |
| 2017/0366921 A1 | 12/2017 | Pflugh et al. |
| 2018/0008159 A1 | 1/2018 | Wang et al. |
| 2018/0091657 A1 | 3/2018 | Brown et al. |
| 2018/0113986 A1 | 4/2018 | Zhu |
| 2018/0113987 A1 | 4/2018 | Zhu |
| 2018/0116537 A1 | 5/2018 | Sullivan et al. |
| 2018/0117299 A1 | 5/2018 | Gustavson et al. |
| 2018/0146922 A1 | 5/2018 | Wang et al. |
| 2018/0192894 A1* | 7/2018 | An ..................... A61B 5/4842 |
| 2018/0220897 A1* | 8/2018 | Meger ................. A61B 5/0205 |
| 2018/0221645 A1 | 8/2018 | Medema et al. |
| 2018/0235537 A1 | 8/2018 | Whiting et al. |
| 2018/0260706 A1 | 9/2018 | Galloway et al. |
| 2018/0301017 A1 | 10/2018 | Dizengof et al. |
| 2018/0322405 A1 | 11/2018 | Fadell et al. |
| 2018/0338731 A1 | 11/2018 | Addison et al. |
| 2018/0348759 A1 | 12/2018 | Freeman et al. |
| 2019/0043616 A1 | 2/2019 | Howard et al. |
| 2019/0066538 A1 | 2/2019 | Chao et al. |
| 2019/0125273 A1 | 5/2019 | Sharma et al. |
| 2019/0197861 A1* | 6/2019 | Tunnell ............... A61B 5/0205 |
| 2019/0275225 A1 | 9/2019 | Brown |
| 2019/0279480 A1 | 9/2019 | Lee et al. |
| 2019/0290216 A1 | 9/2019 | Koyama |
| 2019/0298201 A1 | 10/2019 | Persen et al. |
| 2019/0307328 A1 | 10/2019 | Tran |
| 2019/0328251 A1 | 10/2019 | Jin |
| 2019/0336767 A1 | 11/2019 | Klepfer et al. |
| 2019/0365264 A1 | 12/2019 | Freeman et al. |
| 2019/0365269 A1 | 12/2019 | Jun |
| 2019/0391581 A1 | 12/2019 | Vardaro et al. |
| 2020/0008696 A1 | 1/2020 | Sirendi et al. |
| 2020/0038671 A1 | 2/2020 | Schulhauser et al. |
| 2020/0046241 A1 | 2/2020 | Lam et al. |
| 2020/0069245 A1 | 3/2020 | Zhou |
| 2020/0077892 A1 | 3/2020 | Tran |
| 2020/0085380 A1 | 3/2020 | Sampson |
| 2020/0100693 A1 | 4/2020 | Velo |
| 2020/0113459 A1 | 4/2020 | Jäntti et al. |
| 2020/0146550 A1 | 5/2020 | Tunnell et al. |
| 2020/0160991 A1 | 5/2020 | Smith et al. |
| 2020/0178821 A1 | 6/2020 | Wu et al. |
| 2020/0305737 A1 | 10/2020 | Tseng et al. |
| 2020/0337567 A1 | 10/2020 | McCalmont et al. |
| 2020/0337581 A1 | 10/2020 | Jung et al. |
| 2020/0342966 A1 | 10/2020 | Stern et al. |
| 2020/0352462 A1 | 11/2020 | Pedalty et al. |
| 2020/0352466 A1 | 11/2020 | Chakravarthy et al. |
| 2020/0352522 A1 | 11/2020 | Chakravarthy et al. |
| 2020/0357519 A1 | 11/2020 | Chakravarthy et al. |
| 2020/0373005 A1 | 11/2020 | Halsne et al. |
| 2020/0380840 A1 | 12/2020 | Galarneau et al. |
| 2020/0390354 A1 | 12/2020 | Huegerich et al. |
| 2020/0397308 A1 | 12/2020 | Sarkar et al. |
| 2021/0118562 A1 | 4/2021 | Matos |
| 2021/0121090 A1 | 4/2021 | Weinstein et al. |
| 2021/0138243 A1 | 5/2021 | Zhang et al. |
| 2021/0138254 A1 | 5/2021 | Matos |
| 2021/0154487 A1 | 5/2021 | Bongberg et al. |
| 2021/0169392 A1 | 6/2021 | Albert et al. |
| 2021/0186329 A1 | 6/2021 | Tran |
| 2021/0251578 A1 | 8/2021 | Schulhauser et al. |
| 2021/0259560 A1 | 8/2021 | Venkatraman et al. |
| 2021/0314756 A1 | 10/2021 | Brooks et al. |
| 2021/0338134 A1 | 11/2021 | Chakravarthy et al. |
| 2021/0338138 A1 | 11/2021 | Pedalty et al. |
| 2021/0343132 A1 | 11/2021 | Bonser |
| 2021/0343416 A1 | 11/2021 | Chakravarthy et al. |
| 2021/0345934 A1 | 11/2021 | Landgraf et al. |
| 2021/0353166 A1 | 11/2021 | Sirendi et al. |
| 2021/0401349 A1 | 12/2021 | Schram |
| 2022/0023626 A1 | 1/2022 | Haddad et al. |
| 2022/0031253 A1 | 2/2022 | Burnes et al. |
| 2022/0039729 A1 | 2/2022 | Fontanarava et al. |
| 2022/0051548 A1 | 2/2022 | Pellegrini et al. |
| 2022/0061678 A1 | 3/2022 | Schulhauser et al. |
| 2022/0095982 A1 | 3/2022 | de Saint Victor et al. |
| 2022/0151533 A1 | 5/2022 | Moon |
| 2022/0160250 A1 | 5/2022 | Anderson et al. |
| 2022/0183607 A1 | 6/2022 | Volosin et al. |
| 2022/0218259 A1 | 7/2022 | Laversin et al. |
| 2022/0249026 A1 | 8/2022 | Heneghan et al. |
| 2022/0346725 A1 | 11/2022 | Krause et al. |
| 2023/0263406 A1 | 8/2023 | Stadler et al. |

FOREIGN PATENT DOCUMENTS

| | | |
|---|---|---|
| CN | 105769171 A | 7/2016 |
| CN | 106264518 A | 1/2017 |
| CN | 106562777 A | 4/2017 |
| CN | 107874753 A | 4/2018 |
| CN | 108039203 A | 5/2018 |
| CN | 108324264 A | 7/2018 |
| CN | 207924885 U | 9/2018 |
| CN | 109009047 A | 12/2018 |
| CN | 208460154 U | 2/2019 |
| CN | 109820492 A | 5/2019 |
| CN | 109953753 A | 7/2019 |
| CN | 111667921 A | 9/2020 |
| CN | 112515650 A | 3/2021 |
| CN | 112515651 A | 3/2021 |
| CN | 113080917 A | 7/2021 |
| CN | 113598784 A | 11/2021 |
| CN | 215128553 U | 12/2021 |
| CN | 114711781 A | 7/2022 |
| CN | 217014071 U | 7/2022 |
| EP | 2689363 A2 | 1/2014 |
| ES | 2559263 T3 | 2/2016 |
| FI | 128143 B | 10/2019 |

(56) References Cited

FOREIGN PATENT DOCUMENTS

| | | |
|---|---|---|
| GB | 2569157 A | 6/2019 |
| GB | 2590556 B | 6/2021 |
| GB | 2600710 A | 5/2022 |
| IN | 201811048444 A | 12/2018 |
| JP | 3031277 B2 | 4/2000 |
| JP | 2007289694 A | 11/2007 |
| JP | 2009089883 A | 4/2009 |
| JP | 6764830 A | 12/2018 |
| JP | 2019129954 A | 8/2019 |
| KR | 20030008655 A | 1/2003 |
| KR | 100400212 B1 | 11/2003 |
| KR | 100637566 B1 | 10/2006 |
| KR | 101756787 B1 | 7/2017 |
| KR | 102195189 B1 | 12/2020 |
| MX | 2016007079 A | 11/2017 |
| SU | 442789 A1 | 9/1974 |
| SU | 1042732 A1 | 9/1983 |
| TR | 201719097 A2 | 6/2019 |
| TW | M555707 U | 2/2018 |
| TW | I669097 B | 8/2019 |
| WO | WO 2005021089 A1 | 3/2005 |
| WO | 2010105053 A3 | 1/2011 |
| WO | 2012135059 A2 | 10/2012 |
| WO | 2016034203 A1 | 3/2016 |
| WO | 2017/059274 A1 | 4/2017 |
| WO | 2018202606 A1 | 11/2018 |
| WO | 2019/096876 A1 | 5/2019 |
| WO | 2019110963 A1 | 6/2019 |
| WO | 2020/115747 A1 | 6/2020 |
| WO | 2020155078 A1 | 8/2020 |
| WO | 2020226879 | 11/2020 |
| WO | 2020226881 | 11/2020 |
| WO | 2020226887 | 11/2020 |
| WO | 2021084535 | 5/2021 |
| WO | 2021133360 A1 | 7/2021 |
| WO | 2021181389 A1 | 9/2021 |
| WO | 2022034045 | 2/2022 |
| WO | 2022034480 | 2/2022 |
| WO | 2022070109 | 4/2022 |
| WO | 2022130152 | 6/2022 |

OTHER PUBLICATIONS

Roberts, "Best Buy Makes Deal to Provide its Senior Services on Apple Watch," Star Tribune, Mar. 3, 2021, 2 pp.

Chan et al., "Contactless Cardiac Arrest Detection Using Smart Devices," NPJ Digital Medicine, vol. 2, No. 52, Jun. 19, 2019, 8 pp.

Bayanbay et al., "The Use of Unmanned Aerial Vehicle for Emergency Medical Assistance," 2019 20th International Conference of Young Specialists on Micro/Nanotechnologies and Electron Devices (EDM), Jun. 29-Jul. 3, 2019, pp. 597-600.

"Highlights of the 2020 American Heart Association Guidelines for CPR and ECC," American Heart Association, 2020 (Applicant points out, in accordance with MPEP 609.04(a), that the year of publication, 2020, is sufficiently earlier than the effective U.S. filing date, so that the particular month of publication is not in issue.) 32 p.

Solomon et al., "Sudden Death in Patients with Myocardial Infarction and Left Ventricular Dysfunction, Heart Failure, or Both," vol. 352, No. 25, Jun. 23, 2005, pp. 2581-2588.

Shcherbina et al., "Accuracy in Wrist-Worn, Sensor-Based Measurements of Heart Rate and Energy Expenditure in a Diverse Cohort," Journal of Personalized Medicine, vol. 3, No. 7, May 24, 2017, 12 pp.

Wang et al., "Accuracy of Wrist-Worn Heart Rate Monitors," JAMA Cardiology, vol. 2, No. 1, Jan. 2017, pp. 104-106.

Seshadri et al., "Accuracy of Apple Watch for Detection of Atrial Fibrillation," Circulation, vol. 141, No. 8, Feb. 25, 2020, pp. 702-703.

Tarakji et al., "Using a Novel Wireless System for Monitoring Patients After the Atrial Fibrillation Ablation Procedure: The iTransmit Study," Heart Rhythm Journal, vol. 12, No. 3, Mar. 1, 2015, pp. 554-559.

Instructions for Irregular Rhythm Notification, Apple Inc., Jun. 2020, 154 pp.

Perez et al., "Large-Scale Assessment of a Smartwatch to Identify Atrial Fibrillation," The New England Journal of Medicine, vol. 381, No. 20, Nov. 14, 2019, pp. 1909-1917.

Burke et al., "Smartwatch Detection of Ventricular Tachycardia: Case Series," Heart Rhythm Case Reports, vol. 6, No. 10, Oct. 2020, pp. 801-804.

Ringwald et al., "Smart Watch Recording of Ventricular Tachycardia: Case Study," American Journal of Emergency Medicine, vol. 38, No. 4, Apr. 1, 2020, pp. 849.e3-849.e5.

"Using Apple Watch for Arrhythmia Detection," Apple, Inc., Dec. 2020, 17 pp.

Auer et al., "A Smartwatch to Identify Atrial Fibrillation," The New England Journal of Medicine, vol. 382, No. 10, Mar. 5, 2020, pp. 974-976.

Singh, "Detecting Atrial Fibrillation with with the Apple Watch: Our Clinically Validated Results," https://blog.cardiogr.am/detecting-atrial-fibrillation-with-the-apple-watch-our-clinically-validated-results-ea66163e0fa6, Mar. 21, 2018, 14 pp.

Campion et al., "Watched by Apple," The New England Journal of Medicine, vol. 381, No. 20, Nov. 14, 2019, pp. 1964-1965.

Hwang et al., "Assessing Accuracy of Wrist-Worn Wearable Devices in Measurement of Paroxysmal Supraventricular Tachycardia Heart Rate," Korean Circulation Journal, vol. 49, No. 5, May 2019, pp. 437-445.

Blomberg et al., "Effect of Machine Learning on Dispatcher Recognition of Out-of-Hospital Cardiac Arrest During Calls to Emergency Medical Services A Randomized Clinical Trial," JAMA Network Open, Jan. 6, 2021, 10 pp.

Book of Abstracts, Acta Cardiologica, vol. 76, supp 1, Feb. 22, 2021, 52 pp.

"Cardiac Arrest: An Important Public Health Issue," CDC, retrieved from https://www.cdc.gov/dhdsp/docs/cardiac-arrest-infographic.pdf, on Apr. 23, 2021, 2 pp.

CARES Annual Report 2019, 2019 (Applicant points out, in accordance with MPEP 609.04(a), that the year of publication, 2019, is sufficiently earlier than the effective U.S. filing date, so that the particular month of publication is not in issue.) 48 pp.

Okubo et al., "Characteristics of Paediatric Out-of-Hospital Cardiac Arrest in the United States," Resuscitation, vol. 153, Apr. 27, 2020, pp. 227-233.

"Heart Disease and Stroke Statistics—2019 Update A Report From the American Heart Association," Circulation, vol. 139, Mar. 5, 2019 pp. e56-e528.

Than et al., "Machine Learning to Predict the Likelihood of Acute Myocardial Infarction," Circulation, vol. 140, Sep. 10, 2019, pp. 899-909.

Li et al., "The Current State of Mobile Phone Apps for Monitoring Heart Rate, Heart Rate Variability, and Atrial Fibrillation: Narrative Review," JMIR Mhealth Uhealth, vol. 7, No. 2, e11606, Feb. 15, 2019, 16 pp.

Mell et al., "Emergency Medical Services Response Times in Rural, Suburban, and Urban Areas," JAMA Surgery, vol. 152, No. 10, Oct. 2017, pp. 983-984.

Deo et al., "Epidemiology and Genetics of Sudden Cardiac Death," Circulation, vol. 125, No. 4, Jan. 31, 2012, pp. 620-637.

Rudner et al., "Interrogation of Patient Smartphone Activity Tracker to Assist Arrhythmia Management," Annals of Emergency Medicine, vol. 68, No. 3, Sep. 2016, pp. 292-294.

Goldberger et al., "Risk Stratification for Sudden Cardiac Death a Plan for the Future," Circulation, vol. 129, No. 4, Jan. 28, 2014, pp. 516-526.

Hirano et al., "Early Outcome Prediction for Out-Of-Hospital Cardiac Arrest with Initial Shockable Rhythm Using Machine Learning Models," Resuscitation, vol. 158, No. 145, Jan. 2021, pp. 49-56.

"Monitor your heart rate with Apple Watch," retrieved from https://support.apple.com/en-us/HT204666, on Apr. 23, 2021, 8 pp.

Sudden Cardiac Arrest Meeting the Challenge, The Joint Commission, 2011 (Applicant points out, in accordance with MPEP 609.04(a), that the year of publication, 2011, is sufficiently earlier than

(56) References Cited

OTHER PUBLICATIONS the effective U.S. filing date, so that the particular month of publication is not in issue.) 87 pp.
Bumgarner et al., "Smartwatch Algorithm for Automated Detection of Atrial Fibrillation," Journal of the American College of Cardiology, vol. 71, No. 21, May 29, 2018, pp. 2381-2388.
"Protocol 9, Cardiac or Respiratory Arrest," The EMD Protocol, National Academy Medical Prioity Dispatch System, Accessed on Apr. 23, 2021, 5 pp.
Turakhia et al., "Rationale and Design of a Large-Scale, App-Based Study to Identify Cardiac Arrhythmias Using a Smartwatch: The Apple Heart Study," American Heart Journal, vol. 207, Jan. 2019, pp. 66-75.
Salcido et al., "Have Outcomes After Out of Hospital Cardiac Arrest Improved Over Time?," Circulation: Cardiovascular Quality and Outcomes, vol. 14, No. 3, e007752, Mar. 2021, pp. 290-291.
Zaman et al., "Sudden Cardiac Death Early After Myocardial Infarction Pathogenesis, Risk Stratification, and Primary Prevention," Circulation, vol. 129, No. 23, Jun. 10, 2014, pp. 2426-2435.
Papini et al., "Wearable Monitoring of Sleep-Disordered Breathing: Estimation of the Apnea-Hypopnea Index Using Wrist-Worn Reflective Photoplethysmography," Scientific Reports, vol. 10, No. 13512, Aug. 11, 2020, 15 pp.
Giancaterino et al., "The Smartwatch Will See You Now: Implications of Mass Screening for Atrial Fibrillation," Journal of the American College of Cardiology, vol. 72, No. 12, Sep. 18, 2018, pp. 1433-1434.
Carpenter et al., "Smart-Watches: a Potential Challenger to the Implantable Loop Recorder?," Europace, vol. 18, Feb. 2016, pp. 791-793.
Koshy et al., "Smart Watches for Heart Rate Assessment in Atrial Arrhythmias," International Journal of Cardiology, vol. 266, Sep. 1, 2018, pp. 124-127.
Medtronic Linq II, Medtronic CareLink Network, Jan. 29, 2021, 11 pp.
Waldmann et al., "Temporal Trends of Out-of-Hospital Cardiac Arrests Without Resuscitation Attempt by Emergency Medical Services," Circulation: Cardiovascular Quality and Outcomes, vol. 14, No. e006626, Mar. 2021, pp. 279-289.
Beauchamp et al., "The Use of Wearables in Clinical Trials During Cancer Treatment: Systematic Review," JMIR Mhealth Uhealth, vol. 8, No. 11, e22006, Nov. 2020, 15 pp.
Singhal et al., "The Role of Wearables in Heart Failure," Current Heart Failure Reports, vol. 17, No. 4, Jun. 3, 2020, pp. 125-132.
Samsung Galaxy Watch3 LTE Smartwatch, retrieved from https://www.samsung.com/us/watches/galaxy-watch3/#health, on Apr. 29, 2021, 31 pp.
U.S. Appl. No. 16/593,739, filed Oct. 4, 2019, by Haddad et al.
U.S. Appl. No. 17/101,945, filed Nov. 23, 2020, by Anderson et al.
U.S. Appl. No. 17/301,923, filed Apr. 19, 2021, by Anderson et al.
U.S. Appl. No. 17/006,444, filed Aug. 28, 2020, by Schulhauser.
Dayananda et al., "An Interconnected Architecture for an Emergency Medical Response Unmanned Aerial System," 2017 IEEE/AIAA 36th Digital Avionics Systems Conference (DASC), Sep. 17-21, 2017, pp. 1-6.
U.S. Appl. No. 17/383,170, filed Jul. 22, 2021, by Haddad et al.
U.S. Appl. No. 17/459,713, filed Aug. 27, 2021, by Schulhauser et al.
International Search Report and Written Opinion of International Application No. PCT/US2022/016000, dated May 19, 2022, 13 pp.
U.S. Appl. No. 63/158,189, filed Mar. 8, 2021, naming inventors Stadler et al.
Centers for Disease Control and Prevention et al., "What is v-safe?", Jun. 10, 2022, 1 pp., URL: https://www.cdc.gov/coronavirus/2019-ncov/vaccines/safety/pdfs/v-safe-information-sheet-508c.pdf.
Hause et al., "COVID-19 Vaccine Safety in Adolescents Aged 12-17 Years—United States, Dec. 14, 2020-Jul. 16, 2021", Centers for Disease Control and Prevention, Jul. 30, 2021, 9 pp., URL: https://www.cdc.gov/mmwr/volumes/70/wr/mm703le1.htm.
International Preliminary Report on Patentability from International Application No. PCT/US2022/016000 dated Sep. 21, 2023, 9 pp.
Pulsepoint, "Activate Citizen Response.", Building informed communities, 14 pp., Retrieved from the Internet on Oct. 25, 2021 from URL: ttps://www.pulsepoint.org.
Seifert, "Say hello to Astro, Alexa on wheels", The Verge, Sep. 28, 2021, 18 pp., URL: https://www.theverge.com/2021/9/28/22697244/amazon-astro-home-robot-hands-on-features-price.
Tuohy, "Amazon is now accepting your applications for its home surveillance drone", The Verge, Sep. 29, 2021, 9 pp., URL: https://www.theverge.com/2021/9/28/22692048/ring-always-home-cam-drone-amazon-price-release-date-specs.
U.S. Appl. No. 18/547,105, filed Feb. 16, 2022, naming inventors Stadler et al.
U.S. Appl. No. 18/549,227, filed Feb. 17, 2022, naming inventors Ousdigian et al.
U.S. Appl. No. 18/549,400, filed Feb. 10, 2022, naming inventors Krause et al.
U.S. Appl. No. 18/551,322, filed Feb. 17, naming inventors Neitzell et al.
U.S. Appl. No. 18/552,324, filed Feb. 17, 2022, naming inventors Sarkar et al.
U.S. Appl. No. 63/071,997, filed Aug. 28, 2020, naming inventors Schulhauser et al.
U.S. Appl. No. 63/219,595, filed Jul. 8, 2021, naming inventors Gunderson et al.
U.S. Appl. No. 63/362,451, filed Apr. 4, 2022, naming inventors Galarneau et al.
Volosin et al., "Tachycardia detection performance of implantable loop recorders: results from a large 'real-life' patient cohort and patients with induced ventricular arrhythmias", Europace, vol. 15, No. 8, European Society of Cardiology, Aug. 1, 2013, pp. 1215-1222, URL: https://academic.oup.com/europace/article/15/8/1215/2398708.
Wikipedia, "PulsePoint", Oct. 1, 2021, 12 pp., URL: https://en.wikipedia.org/wiki/PulsePoint.

\* cited by examiner

ACUTE HEALTH EVENT MONITORING

FIELD

This disclosure generally relates to systems including medical devices and, more particularly, to monitoring of patient health using such systems.

BACKGROUND

A variety of devices are configured to monitor physiological signals of a patient. Such devices include implantable or wearable medical devices, as well as a variety of wearable health or fitness tracking devices. The physiological signals sensed by such devices include as examples, electrocardiogram (ECG) signals, respiration signals, perfusion signals, activity and/or posture signals, pressure signals, blood oxygen saturation signals, body composition, and blood glucose or other blood constituent signals. In general, using these signals, such devices facilitate monitoring and evaluating patient health over a number of months or years, outside of a clinic setting.

In some cases, such devices are configured to detect acute health events based on the physiological signals, such as episodes of cardiac arrhythmia, myocardial infarction, stroke, or seizure. Example arrhythmia types include cardiac arrest (e.g., asystole), ventricular tachycardia (VT), and ventricular fibrillation (VF). The devices may store ECG and other physiological signal data collected during a time period including an episode as episode data. Such acute health events are associated with significant rates of death, particularly if not treated quickly.

For example, VF and other malignant tachyarrhythmias are the most commonly identified arrhythmia in sudden cardiac arrest (SCA) patients. If this arrhythmia continues for more than a few seconds, it may result in cardiogenic shock and cessation of effective blood circulation. The survival rate from SCA decreases between 7 and 10 percent for every minute that the patient waits for defibrillation. Consequently, sudden cardiac death (SCD) may result in a matter of minutes.

SUMMARY

In general, the disclosure describes techniques for detection of acute health events, such as sudden cardiac arrest (SCA), by monitoring patient parameter data. More particularly, the disclosure describes techniques for applying rules, which may include one or more machine learning models, to patient parameter data to detect acute health events. The techniques include configuring rules and/or the application of the rules to the patient parameter data in order to improve the efficiency and effectiveness of the detection of acute health events.

For example, processing circuitry may apply a first set of rules to a first set of patient parameter data for a first determination of whether an acute health event is detected. Based on whether one or more context criteria associated with the first determination are satisfied, the processing circuitry may determine whether to apply a second set of rules to second patient parameter data to determine whether the acute health event is detected. The second set of rules and patient parameter data may include more complex rules and/or more patient parameters from additional sensors. Context criteria may include a threshold determination confidence or event likelihood of the first determination, whether user input during or subsequent to the first determination satisfied a criterion, or a threshold power level of a monitoring system. In this manner, devices and systems employing the techniques of this disclosure conserve system resource use associated with the second determination for certain cases in which the context of the first determination suggests it may be less reliable than desired.

In one example, a system comprises processing circuitry and memory. The memory comprises program instructions that, when executed by the processing circuitry, cause the processing circuitry to: apply a first set of rules to first patient parameter data for a first determination of whether sudden cardiac arrest of a patient is detected; determine that one or more context criteria of the first determination are satisfied; and in response to satisfaction of the one or more context criteria, apply a second set of rules to second patient parameter data for a second determination of whether sudden cardiac arrest of the patient is detected. At least the second set of rules comprises a machine learning model, and the second patient parameter data comprises at least one patient parameter that is not included in the first patient parameter data.

In another example, a method comprises by processing circuitry: applying a first set of rules to first patient parameter data for a first determination of whether sudden cardiac arrest of a patient is detected; determining that one or more context criteria of the first determination are satisfied; and in response to satisfaction of the one or more context criteria, applying a second set of rules to second patient parameter data for a second determination of whether sudden cardiac arrest of the patient is detected. At least the second set of rules comprises a machine learning model, and the second patient parameter data comprises at least one patient parameter that is not included in the first patient parameter data.

In another example, anon-transitory computer-readable storage medium comprising instructions that, when executed by processing circuitry, cause the processing circuitry to: apply a first set of rules to first patient parameter data for a first determination of whether sudden cardiac arrest of a patient is detected; determine that a one or more context criteria of the first determination are satisfied; and in response to satisfaction of the context criteria, apply a second set of rules to second patient parameter data for a second determination of whether sudden cardiac arrest of the patient is detected. At least the second set of rules comprises a machine learning model, and the second patient parameter data comprises at least one patient parameter that is not included in the first patient parameter data.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

BRIEF DESCRIPTION OF DRAWINGS

Like reference characters refer to like elements throughout the figures and description.

DETAILED DESCRIPTION

A variety of types of implantable and external devices are configured to detect arrhythmia episodes and other acute health events based on sensed ECGs and, in some cases, other physiological signals. External devices that may be used to non-invasively sense and monitor ECGs and other physiological signals include wearable devices with electrodes configured to contact the skin of the patient, such as patches, watches, rings, necklaces, hearing aids, clothing, car seats, or bed linens. Such external devices may facilitate relatively longer-term monitoring of patient health during normal daily activities.

Implantable medical devices (IMDs) also sense and monitor ECGs and other physiological signals, and detect acute health events such as episodes of arrhythmia, cardiac arrest, myocardial infarction, stroke, and seizure. Example IMDs include pacemakers and implantable cardioverter-defibrillators, which may be coupled to intravascular or extravascular leads, as well as pacemakers with housings configured for implantation within the heart, which may be leadless. Some IMDs do not provide therapy, such as implantable patient monitors. One example of such an IMD is the Reveal LINQ II™ Insertable Cardiac Monitor (ICM), available from Medtronic plc, which may be inserted subcutaneously. Such IMDs may facilitate relatively longer-term monitoring of patients during normal daily activities, and may periodically transmit collected data, e.g., episode data for detected arrhythmia episodes, to a remote patient monitoring system, such as the Medtronic Carelink™ Network.

Figure 1:
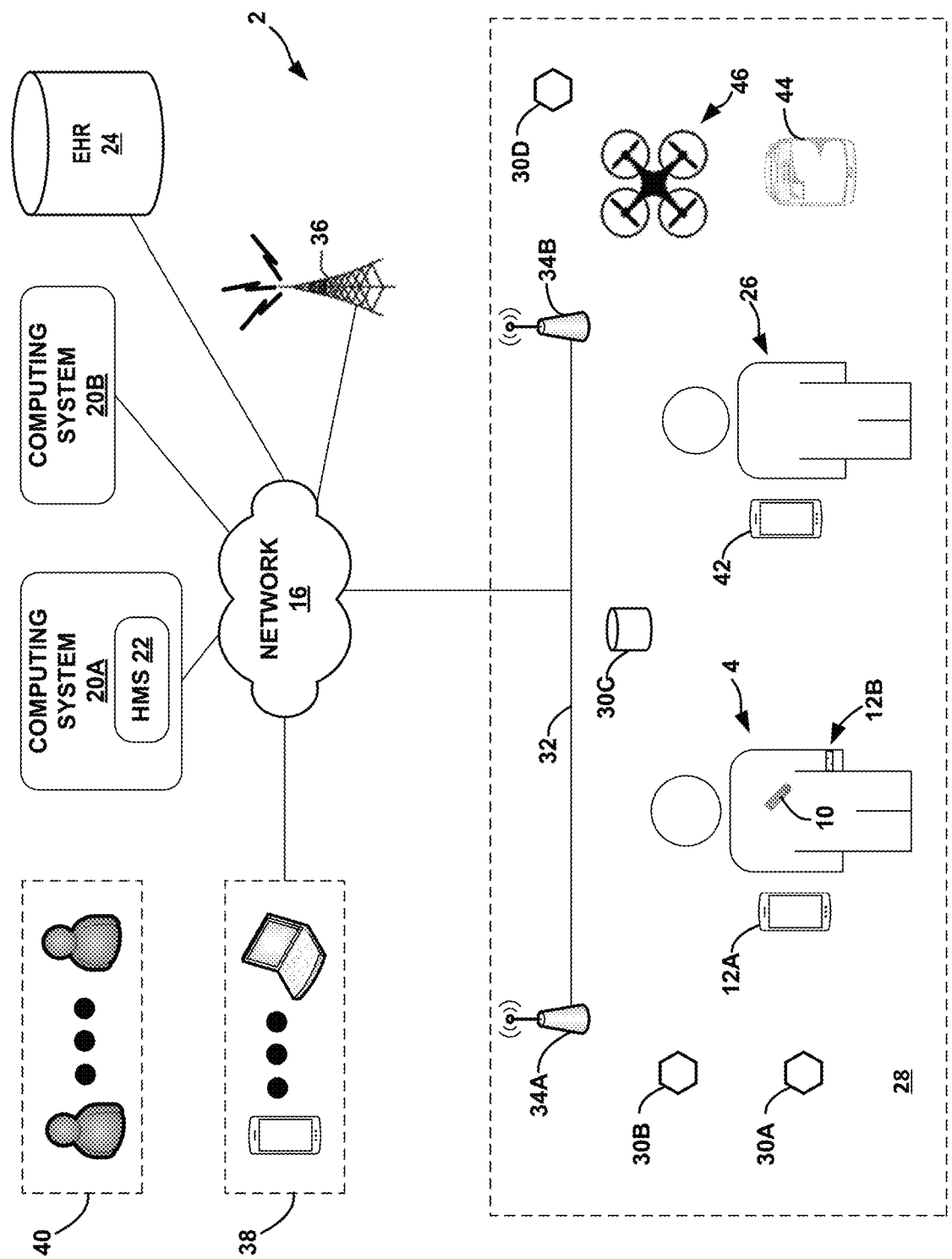
FIG. 1 is a block diagram illustrating an example system configured detect acute health events of a patient, and to respond to such detections, in accordance with one or more techniques of this disclosure.

FIG. 1 is a block diagram illustrating an example system 2 configured detect acute health events of a patient 4, and to respond to such detection, in accordance with one or more techniques of this disclosure. As used herein, the terms "detect," "detection," and the like may refer to detection of an acute health event presently (at the time the data is collected) being experienced by patient 4, as well as detection based on the data that the condition of patient 4 is such that they have a suprathreshold likelihood of experiencing the event within a particular timeframe, e.g., prediction of the acute health event. The example techniques may be used with one or more patient sensing devices, e.g., IMD 10, which may be in wireless communication with one or more patient computing devices, e.g., patient computing devices 12A and 12B (collectively, "patient computing devices 12"). Although not illustrated in FIG. 1, IMD 10 include electrodes and other sensors to sense physiological signals of patient 4, and may collect and store sensed physiological data based on the signals and detect episodes based on the data.

IMD 10 may be implanted outside of a thoracic cavity of patient 4 (e.g., subcutaneously in the pectoral location illustrated in FIG. 1). IMD 10 may be positioned near the sternum near or just below the level of the heart of patient 4, e.g., at least partially within the cardiac silhouette. In some examples, IMD 10 takes the form of the LINQ II™ ICM. Although described primarily in the context of examples in which IMD 10 takes the form of an ICM, the techniques of this disclosure may be implemented in systems including any one or more implantable or external medical devices, including monitors, pacemakers, defibrillators, wearable external defibrillators, neurostimulators, or drug pumps. Furthermore, although described primarily in the context of examples including a single implanted patient sensing device, in some examples a system includes one or more patient sensing devices, which may be implanted within patient 4 or external to (e.g., worn by) patient 4. For example, a system with two IMDs 10 may capture different values of a common patient parameter with different resolution/accuracy based on their respective locations. In some examples, instead of or in addition to two IMDs 10, system 2 may include a ventricular assist device or WAED in addition to IMD 10.

Patient computing devices 12 are configured for wireless communication with IMD 10. Computing devices 12 retrieve event data and other sensed physiological data from IMD 10 that was collected and stored by the IMD. In some examples, computing devices 12 take the form of personal computing devices of patient 4. For example, computing device 12A may take the form of a smartphone of patient 4, and computing device 12B may take the form of a smartwatch or other smart apparel of patient 4. In some examples, computing devices 12 may be any computing device configured for wireless communication with IMD 10, such as a desktop, laptop, or tablet computer. Computing devices 12 may communicate with IMD 10 and each other according to the Bluetooth® or Bluetooth® Low Energy (BLE) protocols, as examples. In some examples, only one of computing devices 12, e.g., computing device 12A, is configured for communication with IMD 10, e.g., due to execution of software (e.g., part of a health monitoring application as described herein) enabling communication and interaction with an IMD.

In some examples, computing device(s) 12, e.g., wearable computing device 12B in the example illustrated by FIG. 1, may include electrodes and other sensors to sense physiological signals of patient 4, and may collect and store physiological data and detect episodes based on such signals. Computing device 12B may be incorporated into the apparel of patient 14, such as within clothing, shoes, eyeglasses, a watch or wristband, a hat, etc. In some examples, computing device 12B is a smartwatch or other accessory or peripheral for a smartphone computing device 12A.

One or more of computing devices 12 may be configured to communicate with a variety of other devices or systems via a network 16. For example, one or more of computing devices 12 may be configured to communicate with one or more computing systems, e.g., computing systems 20A and 20B (collectively, "computing systems 20") via network 16. Computing systems 20A and 20B may be respectively managed by manufacturers of IMD 10 and computing devices 12 to, for example, provide cloud storage and analysis of collected data, maintenance and software services, or other networked functionality for their respective devices and users thereof. Computing system 20A may comprise, or may be implemented by, the Medtronic Carelink™ Network, in some examples. In the example illustrated by FIG. 1, computing system 20A implements a health monitoring system (HMS) 22, although in other examples, either of both of computing systems 20 may implement HMS 22. As will be described in greater detail below, HMS 22 facilities detection of acute health events of patient 4 by system 2, and the responses of system 2 to such acute health events.

Computing device(s) 12 may transmit data, including data retrieved from IMD 10, to computing system(s) 20 via network 16. The data may include sensed data, e.g., values of physiological parameters measured by IMD 10 and, in some cases one or more of computing devices 12, data regarding episodes of arrhythmia or other acute health events detected by IMD 10 and computing device(s) 12, and other physiological signals or data recorded by IMD 10 and/or computing device(s) 12. HMS 22 may also retrieve data regarding patient 4 from one or more sources of electronic health records (EHR) 24 via network. EHR 24 may include data regarding historical (e.g., baseline) physiological parameter values, previous health events and treatments, disease states, comorbidities, demographics, height, weight, and body mass index (BMI), as examples, of patients including patient 4. HMS 22 may use data from EHR 24 to configure algorithms implemented by IMD 10 and/or computing devices 12 to detect acute health events for patient 4. In some examples, HMS 22 provides data from EHR 24 to computing device(s) 12 and/or IMD 10 for storage therein and use as part of their algorithms for detecting acute health events.

Network 16 may include one or more computing devices, such as one or more non-edge switches, routers, hubs, gateways, security devices such as firewalls, intrusion detection, and/or intrusion prevention devices, servers, cellular base stations and nodes, wireless access points, bridges, cable modems, application accelerators, or other network devices. Network 16 may include one or more networks administered by service providers, and may thus form part of a large-scale public network infrastructure, e.g., the Internet. Network 16 may provide computing devices and systems, such as those illustrated in FIG. 1, access to the Internet, and may provide a communication framework that allows the computing devices and systems to communicate with one another. In some examples, network 16 may include a private network that provides a communication framework that allows the computing devices and systems illustrated in FIG. 1 to communicate with each other, but isolates some of the data flows from devices external to the private network for security purposes. In some examples, the communications between the computing devices and systems illustrated in FIG. 1 are encrypted.

As will be described herein, IMD 10 may be configured to detect acute health events of patient 4, such as SCA, based on data sensed by IMD 10 and, in some cases, other data, such as data sensed by computing devices 12A and/or 12B, and data from EHR 24. To detect acute health events, IMD 10 may apply rules to the data, which may be referred to as patient parameter data. In response to detection of an acute health event, IMD 10 may wirelessly transmit a message to one or both of computing devices 12A and 12B. The message may indicate that IMD 10 detected an acute health event of the patient. The message may indicate a time that IMD 10 detected the acute health event. The message may include physiological data collected by IMD 10, e.g., data which lead to detection of the acute health event, data prior to detection of the acute health event, and/or real-time or more recent data collected after detection of the acute health event. The physiological data may include values of one or more physiological parameters and/or digitized physiological signals. Examples of acute health events are SCA, a ventricular fibrillation, a ventricular tachycardia, myocardial infarction, a pause in heart rhythm (asystole), or Pulseless Electrical Activity (PEA), acute respiratory distress syndrome (ARDS), a stroke, a seizure, or a fall.

In some examples, the detection of the acute health event by IMD 10 may include multiple phases. For example, IMD 10 may complete an initial detection of the acute health event, e.g., SCA or tachyarrhythmia, and initiate wireless communication, e.g., Bluetooth® or Bluetooth Low Energy®, with computing device(s) 12 in response to the initial detection. The initial detection may occur five to ten seconds after onset of the acute health event, for example. IMD 10 may continue monitoring to determine whether the acute health event is sustained, e.g., a sustained detection of SCA or tachyarrhythmia. In some examples, IMD 10 may use more patient parameters and/or different rules to determine whether event is sustained or otherwise confirm detection.

Initiating communication with computing device(s) 12 in response to an initial detection may facilitate the communication being established at the time the acute health event is confirmed as sustained. To conserve power of IMD 10 and computing device(s) 12, IMD 10 may wait to send the message, e.g., including sensed data associated with the acute health event, until it is confirmed as sustained, which may be determined about thirty seconds after onset of the event, or after a longer period of time. Less urgent events may have longer confirmation phases and may be alerted with less urgency, such being alerted as health care events rather than acute health events. However, the initiation of communication after initial detection may still benefit less urgent events. Conserving power may be significant in the case of non-rechargeable IMDs to prolong their life prior to needing surgery for replacement, as well as for rechargeable IMDs or external devices to reduce recharge frequency.

In response to the message from IMD 10, computing device(s) 12 may output an alarm that may be visual and/or audible, and configured to immediately attract the attention of patient 4 or any person in environment 28 with patient 4, e.g., a bystander 26. Additionally or alternatively, computing device(s) 12 may transmit an alert or alarm message to devices and users outside the visible/audio range of computing device(s) 12, e.g., to IoT devices 30, bystander computing device 42, or HMS 22. Environment 28 may be a home, office, or place of business, or public venue, as examples. An alert or alarm message sent to HMS 22 via network 16, or other messages sent by computing device(s) 12, may include the data received from IMD 10 and, in some cases, additional data collected by computing device(s) 12 or other devices in response to the detection of the acute health event by IMD 10. For example, the message may include a location of patient 4 determined by computing device(s) 12. In some examples, computing device(s) 12 may further configure or change the content of alert or alarm messages based on the location of patient 4, e.g., different messages may be sent depending on whether patient 4 is at home, another residence, an office or business, a public location, or in a health care facility. The health care needed by patient, and thus the messaging of system 2, may vary depending on the location of patient 4.

Other devices in the environment 28 of patient 4 may also be configured to output alarms or take other actions to attract the attention of patient 4 and, possibly, a bystander 26, or to otherwise facilitate the delivery of care to patient 4. For example, environment 28 may include one or more Internet of Things (IoT) devices, such as IoT devices 30A-30D (collectively "IoT devices 30") illustrated in the example of FIG. 1. IoT devices 30 may include, as examples, so called "smart" speakers, cameras, televisions, lights, locks, thermostats, appliances, actuators, controllers, or any other smart home (or building) devices. In the example of FIG. 1, IoT device 30C is a smart speaker and/or controller, which may include a display. IoT devices 30 may provide audible and/or visual alarms when configured with output devices to do so. As other examples, IoT devices 30 may cause smart lights throughout environment 28 to flash or blink and unlock doors. In some examples, IoT devices 30 that include cameras or other sensors may activate those sensors to collect data regarding patient 4, e.g., for evaluation of the condition of patient 4.

Computing device(s) 12 may be configured to wirelessly communicate with IoT devices 30 to cause IoT devices 30 to take the actions described herein. In some examples, HMS 22 communicates with IoT devices 30 via network 16 to cause IoT devices 30 to take the actions described herein, e.g., in response to receiving the alert message from computing device(s) 12 as described above. In some examples, IMD 10 is configured to communicate wirelessly with one or more of IoT devices 30, e.g., in response to detection of an acute health event when communication with computing devices 12 is unavailable. In such examples, IoT device(s) 30 may be configured to provide some or all of the functionality ascribed to computing devices 12 herein.

Environment 28 includes computing facilities, e.g., a local network 32, by which computing devices 12, IoT devices 30, and other devices within environment 28 may communicate via network 16, e.g., with HMS 22. For example, environment 28 may be configured with wireless technology, such as IEEE 802.11 wireless networks, IEEE 802.15 ZigBee networks, an ultra-wideband protocol, near-field communication, or the like. Environment 28 may include one or more wireless access points, e.g., wireless access points 34A and 34B (collectively, "wireless access points 34") that provide support for wireless communications throughout environment 28. Additionally or alternatively, e.g., when local network is unavailable, computing devices 12, IoT devices 30, and other devices within environment 28 may be configured to communicate with network 16, e.g., with HMS 22, via a cellular base station 36 and a cellular network.

Computing device(s) 12, and in some examples IoT device(s) 30, may include input devices and interfaces to allow a user to override the alarm in the event the detection of the acute health event by IMD 10 was false. In some examples, one or more of computing device(s) 12 and IoT device(s) 30 may implement an event assistant. The event assistant may provide a conversational interface for patient 4 and/or bystander 26 to exchange information with the computing device or IoT device. The event assistant may query the user regarding the condition of patient 4 in response to receiving the alert message from IMD 10. Responses from the user may be used to confirm or override detection of the acute health event by IMD 10, or to provide additional information about the acute health event or the condition of patient 4 more generally that may improve the efficacy of the treatment of patient 4. For example, information received by the event assistant may be used to provide an indication of severity or type (differential diagnosis) for the acute health event. The event assistant may use natural language processing and context data to interpret utterances by the user. In some examples, in addition to receiving responses to queries posed by the assistant, the event assistant may be configured to respond to queries posed by the user. For example, patient 4 may indicate that they feel dizzy and ask the event assistant, "how am I doing?".

In some examples, computing device(s) 12 and/or HMS 22 may implement one or more algorithms to evaluate the sensed physiological data received from IMD 10, and in some cases additional physiological or other patient parameter data sensed or otherwise collected by the computing device(s) or IoT devices 30, to confirm or override the detection of the acute health event by IMD 10. In some examples, computing device(s) 12 and/or computing system(s) 20 may have greater processing capacity than IMD 10, enabling more complex analysis of the data. In some examples, the computing device(s) 12 and/or HMS 22 may apply the data to a machine learning model or other artificial intelligence developed algorithm, e.g., to determine whether the data is sufficiently indicative of the acute health event.

In examples in which computing device(s) 12 are configured perform an acute health event confirmation analysis, computing device(s) 12 may transmit alert messages to HMS 22 and/or IoT devices 30 in response to confirming the acute health event. In some examples, computing device(s) 12 may be configured to transmit the alert messages prior to completing the confirmation analysis, and transmit cancellation messages in response to the analysis overriding the detection of the acute health event by IMD 10. HMS 22 may be configured to perform a number of operations in response to receiving an alert message from computing device(s) 12 and/or IoT device(s) 30. HMS 22 may be configured to cancel such operations in response to receiving a cancellation message from computing device(s) 12 and/or IoT device(s) 30.

For example, HMS 22 may be configured to transmit alert messages to one or computing devices 38 associated with one or more care providers 40 via network 16. Care providers may include emergency medical systems (EMS) and hospitals, and may include particular departments within a hospital, such as an emergency department, catheterization lab, or a stroke response department. Computing devices 38 may include smartphones, desktop, laptop, or tablet computers, or workstations associated with such systems or entities, or employees of such systems or entities. The alert messages may include any of the data collected by IMD 10, computing device(s) 12, and IoT device(s) 30, including sensed physiological data, time of the acute health event, location of patient 4, and results of the analysis by IMD 10, computing device(s) 12, IoT device(s) 30, and/or HMS 22. The information transmitted from HMS 22 to care providers 40 may improve the timeliness and effectiveness of treatment of the acute health event of patient 4 by care providers 40. In some examples, instead of or in addition to HMS 22 providing an alert message to one or more computing devices 38 associated with an EMS care provider 40, computing device(s) 12 and/or IoT devices 30 may be configured to automatically contact EMS, e.g., autodial 911, in response to receiving an alert message from IMD 10. Again, such operations may be cancelled by patient 4, bystander 26, or another user via a user interface of computing device(s) 12 or IoT device(s) 30, or automatically cancelled by computing device(s) 12 based on a confirmatory analysis performed by the computing device(s) overriding the detection of the acute health event by IMD 10.

Similarly, HMS 22 may be configured to transmit an alert message to computing device 42 of bystander 26, which may improve the timeliness and effectiveness of treatment of the acute health event of patient 4 by bystander 26. Computing device 42 may be similar to computing devices 12 and computing devices 38, e.g., a smartphone. In some examples, HMS 22 may determine that bystander 26 is proximate to patient 4 based on a location of patient 4, e.g., received from computing device(s) 12, and a location of computing device 42, e.g., reported to HMS 22 by an application implemented on computing device 42. In some examples, HMS 22 may transmit the alert message to any computing devices 42 in an alert area determined based on the location of patient 4, e.g., by transmitting the alert message to all computing devices in communication with base station 36, using any of the networking methods described herein.

In some examples, the alert message to bystander 26 may be configured to assist a layperson in treating patient. For example, the alert message to bystander 26 may include a location (and in some cases a description) of patient 4, the general nature of the acute health event, directions for providing care to patient 4, such as directions for providing cardio-pulmonary resuscitation (CPR), a location of nearby medical equipment for treatment of patient 4, such as an automated external defibrillator (AED) 44 or life vest, and instructions for use of the equipment. In some examples, computing device(s) 12, IoT device(s) 30, and/or computing device 42 may implement an event assistant configured to use natural language processing and context data to provide a conversational interface for bystander 42. The assistant may provide bystander 26 with directions for providing care to patient 4, and respond to queries from bystander 26 about how to provide care to patient 4.

In some examples, HMS 22 may mediate bi-directional audio (and in some cases video) communication between care providers 40 and patient 4 or bystander 26. Such communication may allow care providers 40 to evaluate the condition of patient 4, e.g., through communication with patient 4 or bystander 26, or through use of a camera or other sensors of the computing device or IoT device, in advance of the time they will begin caring for the patient, which may improve the efficacy of care delivered to the patient. Such communication may also allow the care providers to instruct bystander 42 regarding first responder treatment of patient 4.

In some examples, HMS 22 may control dispatch of a drone 46 to environment 28, or a location near environment 28 or patient 4. Drone 46 may be a robot and/or unmanned aerial vehicle (UAV). Drone 46 may be equipped with a number of sensors and/or actuators to perform a number of operations. For example, drone 46 may include a camera or other sensors to navigate to its intended location, identify patient 4 and, in some cases, bystander 26, and to evaluate a condition of patient. In some examples, drone 46 may include user interface devices to communicate with patient 4 and/or bystander 26. In some examples, drone 46 may provide directions to bystander 26, to the location of patient 4 and regarding how to provide first responder care, such as CPR, to patient 4. In some examples, drone 46 may carry medical equipment, e.g., AED 44, and/or medication to the location of patient 4.

Any of IMD 10, computing device(s) 12, IoT device(s) 30, computing device(s) 38 and 42, AED 44, drone 46, or HMS 22 may, individually or in any combination, perform the operations described herein for detection of acute health events, such as SCA, by applying rules, which may include one or more machine learning models, to patient parameter data to detect acute health events. For example, one of these devices, or more than one of them in cooperation, may apply a first set of rules to a first set of patient parameter data for a first determination of whether an acute health event is detected and, based on whether one or more context criteria associated with the first determination are satisfied, determine whether to apply a second set of rules to second patient parameter data to determine whether the acute health event is detected.

Figure 2:
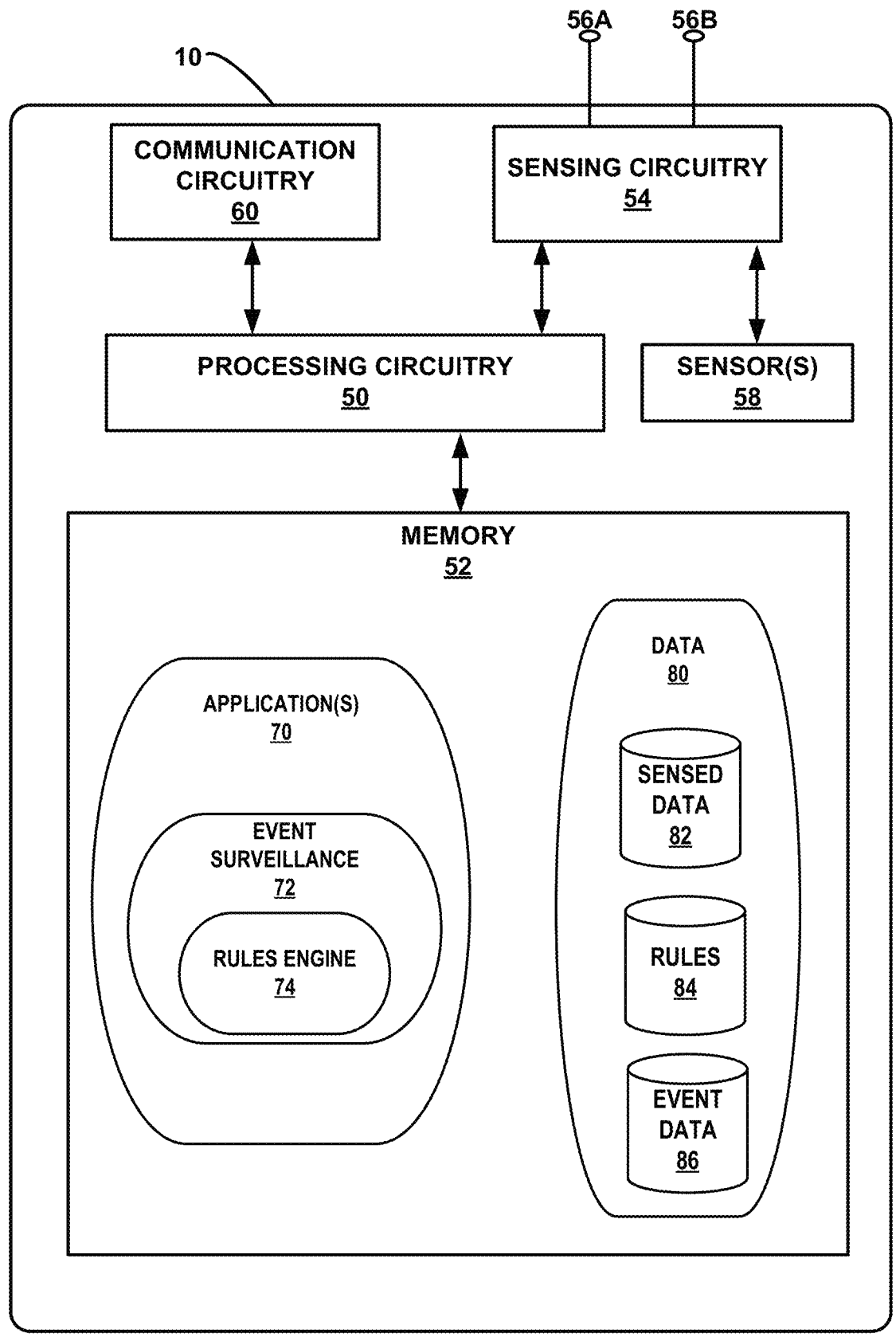
FIG. 2 is a block diagram illustrating an example configuration of a patient sensing device that operates in accordance with one or more techniques of the present disclosure.

FIG. 2 is a block diagram illustrating an example configuration of IMD 10 of FIG. 1. As shown in FIG. 2, IMD 10 includes processing circuitry 50, memory 52, sensing circuitry 54 coupled to electrodes 56A and 56B (hereinafter, "electrodes 56") and one or more sensor(s) 58, and communication circuitry 60.

Processing circuitry 50 may include fixed function circuitry and/or programmable processing circuitry. Processing circuitry 50 may include any one or more of a microprocessor, a controller, a graphics processing unit (GPU), a tensor processing unit (TPU), a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more GPUs, one or more TPUs, one or more DSPs, one or more ASICs, or one or more FPGAs, as well as other discrete or integrated logic circuitry. The functions attributed to processing circuitry 50 herein may be embodied as software, firmware, hardware, or any combination thereof. In some examples, memory 53 includes computer-readable instructions that, when executed by processing circuitry 50, cause IMD 10 and processing circuitry 50 to perform various functions attributed herein to IMD 10 and processing circuitry 50. Memory 53 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Sensing circuitry 54 may monitor signals from electrodes 56 in order to, for example, monitor electrical activity of a heart of patient 4 and produce ECG data for patient 4. In some examples, processing circuitry 50 may identify features of the sensed ECG, such as heart rate, heart rate variability, T-wave alternans, intra-beat intervals (e.g., QT intervals), and/or ECG morphologic features, to detect an episode of cardiac arrhythmia of patient 4. Example Processing circuitry 50 may store the digitized ECG and features of the ECG used to detect the arrhythmia episode in memory 52 as episode data for the detected arrhythmia episode.

In some examples, sensing circuitry 54 measures impedance, e.g., of tissue proximate to IMD 10, via electrodes 56. The measured impedance may vary based on respiration, cardiac pulse or flow, and a degree of perfusion or edema. Processing circuitry 50 may determine physiological data relating to respiration, cardiac pulse or flow, perfusion, and/or edema based on the measured impedance.

In some examples, IMD 10 includes one or more sensors 58, such as one or more accelerometers, gyroscopes, microphones, optical sensors, temperature sensors, pressure sensors, and/or chemical sensors. In some examples, sensing circuitry 52 may include one or more filters and amplifiers for filtering and amplifying signals received from one or more of electrodes 56 and/or sensors 58. In some examples, sensing circuitry 54 and/or processing circuitry 50 may include a rectifier, filter and/or amplifier, a sense amplifier, comparator, and/or analog-to-digital converter. Processing circuitry 50 may determine physiological data, e.g., values of physiological parameters of patient 4, based on signals from sensors 58, which may be stored in memory 52. Patient parameters determined from signals from sensors 58 may include oxygen saturation, glucose level, stress hormone level, heart sounds, body motion, body posture, or blood pressure.

Memory 52 may store applications 70 executable by processing circuitry 50, and data 80. Applications 70 may include an acute health event surveillance application 72. Processing circuitry 50 may execute event surveillance application 72 to detect an acute health event of patient 4 based on combination of one or more of the types of physiological data described herein, which may be stored as sensed data 82. In some examples, sensed data 82 may additionally include patient parameter data sensed by other devices, e.g., computing device(s) 12 or IoT device(s) 30, and received via communication circuitry 60. Event surveillance application 72 may be configured with a rules engine 74. Rules engine 74 may apply rules 84 to sensed data 82. Rules 84 may include one or more models, algorithms, decision trees, and/or thresholds. In some cases, rules 84 may be developed based on machine learning, e.g., may include one or more machine learning models.

As examples, event surveillance application 72 may detect SCA, a ventricular fibrillation, a ventricular tachycardia, supra-ventricular tachycardia (e.g., conducted atrial fibrillation), ventricular asystole, or a myocardial infarction based on an ECG and/or other patient parameter data indicating the electrical or mechanical activity of the heart of patient 4. In some examples, event surveillance application 72 may detect stroke based on such cardiac activity data. In some examples, sensing circuitry 54 may detect brain activity data, e.g., an electroencephalogram (EEG) via electrodes 56, and event surveillance application 72 may detect stroke or a seizure based on the brain activity alone, or in combination with cardiac activity data or other physiological data. In some examples, event surveillance application 72 detects whether the patient has fallen based on data from an accelerometer alone, or in combination with other physiological data. When event surveillance application 72 detects an acute health event, event surveillance application 72 may store the sensed data 82 that lead to the detection (and in some cases a window of data preceding and/or following the detection) as event data 86.

In some examples, in response to detection of an acute health event, processing circuitry 50 transmits, via communication circuitry 60, event data 86 for the event to computing device(s) 12 (FIG. 1). This transmission may be included in a message indicating the acute health event, as described herein. Transmission of the message may occur on an ad hoc basis and as quickly as possible. Communication circuitry 60 may include any suitable hardware, firmware, software, or any combination thereof for wirelessly communicating with another device, such as computing devices 12 and/or IoT devices 30.

Figure 3:
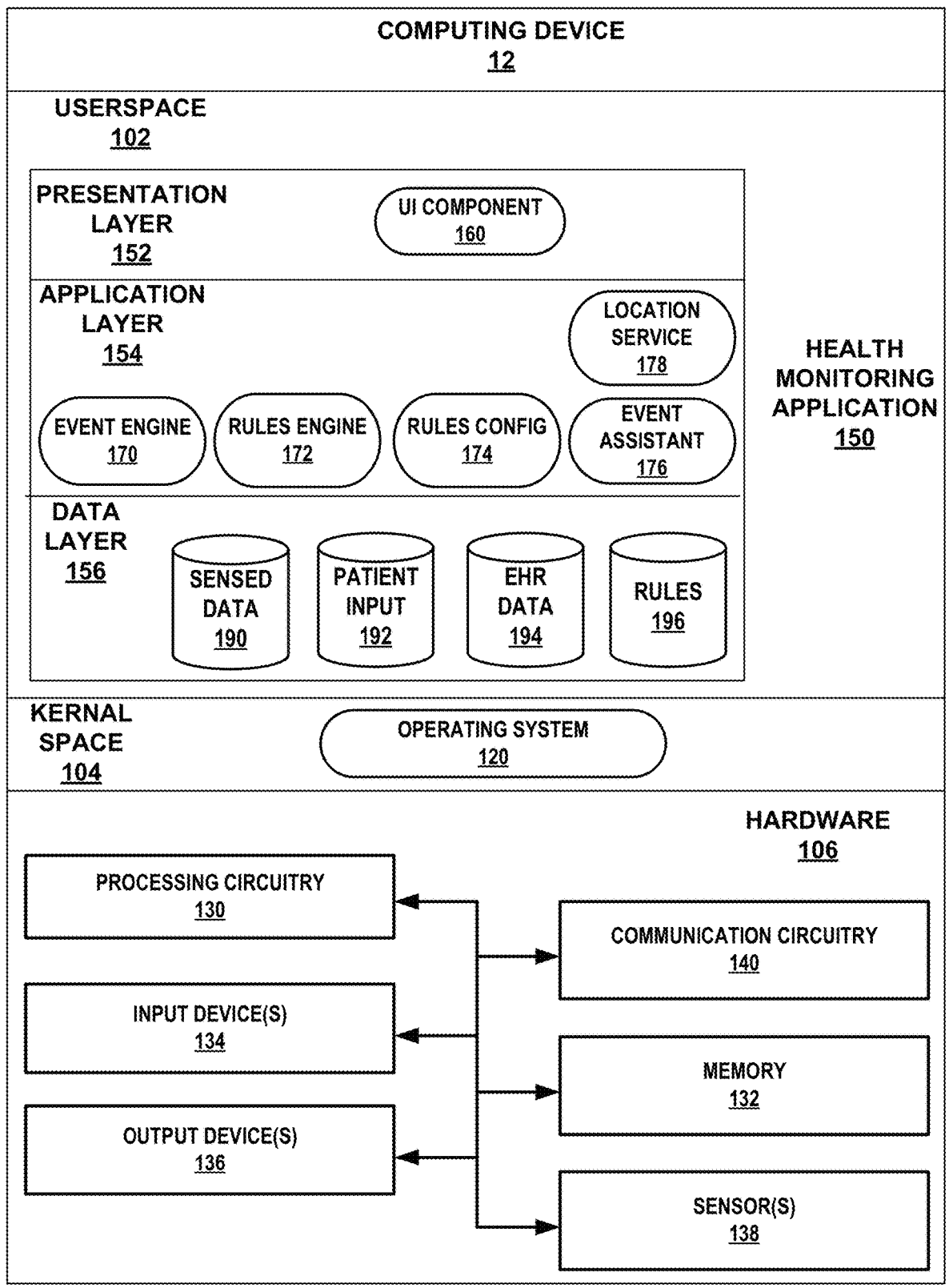
FIG. 3 is block diagram illustrating an example configuration of a computing device that operates in accordance with one or more techniques of the present disclosure.

FIG. 3 is a block diagram illustrating an example configuration of a computing device 12 of patient 4, which may correspond to either (or both operating in coordination) of computing devices 12A and 12B illustrated in FIG. 1. In some examples, computing device 12 takes the form of a smartphone, a laptop, a tablet computer, a personal digital assistant (PDA), a smartwatch or other wearable computing device. In some examples, IoT devices 30, computing devices 38 and 42, AED 44, and/or drone 46 may be configured similarly to the configuration of computing device 12 illustrated in FIG. 3.

As shown in the example of FIG. 3, computing device 12 may be logically divided into user space 102, kernel space 104, and hardware 106. Hardware 106 may include one or more hardware components that provide an operating environment for components executing in user space 102 and kernel space 104. User space 102 and kernel space 104 may represent different sections or segmentations of memory, where kernel space 104 provides higher privileges to processes and threads than user space 102. For instance, kernel space 104 may include operating system 120, which operates with higher privileges than components executing in user space 102.

As shown in FIG. 3, hardware 106 includes processing circuitry 130, memory 132, one or more input devices 134, one or more output devices 136, one or more sensors 138, and communication circuitry 140. Although shown in FIG. 3 as a stand-alone device for purposes of example, computing device 12 may be any component or system that includes processing circuitry or other suitable computing environment for executing software instructions and, for example, need not necessarily include one or more elements shown in FIG. 3.

Processing circuitry 130 is configured to implement functionality and/or process instructions for execution within computing device 12. For example, processing circuitry 130 may be configured to receive and process instructions stored in memory 132 that provide functionality of components included in kernel space 104 and user space 102 to perform one or more operations in accordance with techniques of this disclosure. Examples of processing circuitry 130 may include, any one or more microprocessors, controllers, GPUs, TPUs, DSPs, ASICs, FPGAs, or equivalent discrete or integrated logic circuitry.

Memory 132 may be configured to store information within computing device 12, for processing during operation of computing device 12. Memory 132, in some examples, is described as a computer-readable storage medium. In some examples, memory 132 includes a temporary memory or a volatile memory. Examples of volatile memories include random access memories (RAM), dynamic random access memories (DRAM), static random access memories (SRAM), and other forms of volatile memories known in the art. Memory 132, in some examples, also includes one or more memories configured for long-term storage of information, e.g. including non-volatile storage elements. Examples of such non-volatile storage elements include magnetic hard discs, optical discs, floppy discs, flash memories, or forms of electrically programmable memories (EPROM) or electrically erasable and programmable (EEPROM) memories. In some examples, memory 132 includes cloud-associated storage.

One or more input devices 134 of computing device 12 may receive input, e.g., from patient 4 or another user. Examples of input are tactile, audio, kinetic, and optical input. Input devices 134 may include, as examples, a mouse, keyboard, voice responsive system, camera, buttons, control pad, microphone, presence-sensitive or touch-sensitive component (e.g., screen), or any other device for detecting input from a user or a machine.

One or more output devices 136 of computing device 12 may generate output, e.g., to patient 4 or another user. Examples of output are tactile, haptic, audio, and visual output. Output devices 134 of computing device 12 may include a presence-sensitive screen, sound card, video graphics adapter card, speaker, cathode ray tube (CRT)

monitor, liquid crystal display (LCD), light emitting diodes (LEDs), or any type of device for generating tactile, audio, and/or visual output.

One or more sensors 138 of computing device 12 may sense physiological parameters or signals of patient 4. Sensor(s) 138 may include electrodes, accelerometers (e.g., 3-axis accelerometers), an optical sensor, impedance sensors, temperature sensors, pressure sensors, heart sound sensors (e.g., microphones), and other sensors, and sensing circuitry (e.g., including an ADC), similar to those described above with respect to IMD 10 and FIG. 2.

Communication circuitry 140 of computing device 12 may communicate with other devices by transmitting and receiving data. Communication circuitry 140 may include a network interface card, such as an Ethernet card, an optical transceiver, a radio frequency transceiver, or any other type of device that can send and receive information. For example, communication circuitry 140 may include a radio transceiver configured for communication according to standards or protocols, such as 3G, 4G, 5G, WiFi (e.g., 802.11 or 802.15 ZigBee), Bluetooth®, or Bluetooth® Low Energy (BLE).

As shown in FIG. 3, health monitoring application 150 executes in user space 102 of computing device 12. Health monitoring application 150 may be logically divided into presentation layer 152, application layer 154, and data layer 156. Presentation layer 152 may include a user interface (UI) component 160, which generates and renders user interfaces of health monitoring application 150.

Application layer 154 may include, but is not limited to, an event engine 170, rules engine 172, rules configuration component 174, event assistant 176, and location service 178. Event engine 172 may be responsive to receipt of an alert transmission from IMD 10 indicating that IMD 10 detected an acute health event. Event engine 172 may control performance of any of the operations in response to detection of an acute health event ascribed herein to computing device 12, such as activating an alarm, transmitting alert messages to HMS 22, controlling IoT devices 30, and analyzing data to confirm or override the detection of the acute health event by IMD 10.

Rules engine 174 analyzes sensed data 190, and in some examples, patient input 192 and/or EHR data 194, to determine whether there is a sufficient likelihood that patient 4 is experiencing the acute health event detected by IMD 10. Sensed data 190 may include data received from IMD 10 as part of the alert transmission, additional data transmitted from IMD 10, e.g., in "real-time," and physiological and other data related to the condition of patient 4 collected by, for example, computing device(s) 12 and/or IoT devices 30. As examples sensed data 190 from computing device(s) 12 may include one or more of: activity levels, walking/running distance, resting energy, active energy, exercise minutes, quantifications of standing, body mass, body mass index, heart rate, low, high, and/or irregular heart rate events, heart rate variability, walking heart rate, heart beat series, digitized ECG, blood oxygen saturation, blood pressure (systolic and/or diastolic), respiratory rate, maximum volume of oxygen, blood glucose, peripheral perfusion, and sleep patterns.

Patient input 192 may include responses to queries posed by health monitoring application 150 regarding the condition of patient 4, input by patient 4 or another user, such as bystander 26. The queries and responses may occur responsive to the detection of the event by IMD 10, or may have occurred prior to the detection, e.g., as part long-term monitoring of the health of patient 4. User recorded health data may include one or more of: exercise and activity data, sleep data, symptom data, medical history data, quality of life data, nutrition data, medication taking or compliance data, allergy data, demographic data, weight, and height. EHR data 194 may include any of the information regarding the historical condition or treatments of patient 4 described above. EHR data 194 may relate to history of SCA, tachyarrhythmia, myocardial infarction, stroke, seizure, one or more disease states, such as status of heart failure chronic obstructive pulmonary disease (COPD), renal dysfunction, or hypertension, aspects of disease state, such as ECG characteristics, cardiac ischemia, oxygen saturation, lung fluid, activity, or metabolite level, genetic conditions, congenital anomalies, history of procedures, such as ablation or cardioversion, and healthcare utilization. EHR data 194 may also include cardiac indicators, such as ejection fraction and left-ventricular wall thickness. EHR data 194 may also include demographic and other information of patient 4, such as age, gender, race, height, weight, and BMI.

Rules engine 172 may apply rules 196 to the data. Rules 196 may include one or more models, algorithms, decision trees, and/or thresholds. In some cases, rules 196 may be developed based on machine learning, e.g., may include one or more machine learning models. In some examples, rules 196 and the operation of rules engine 172 may provide a more complex analysis the patient parameter data, e.g., the data received from IMD 10, than is provided by rules engine 74 and rules 84. In examples in which rules 196 include one or more machine learning models, rules engine 172 may apply feature vectors derived from the data to the model(s).

Rules configuration component 174 may be configured to modify rules 196 (and in some examples rules 84) based on feedback indicating whether the detections and confirmations of acute health events by IMD 10 and computing device 12 were accurate. The feedback may be received from patient 4, or from care providers 40 and/or EHR 24 via HMS 22. In some examples, rules configuration component 174 may utilize the data sets from true and false detections and confirmations for supervised machine learning to further train models included as part of rules 196.

Rules configuration component 174, or another component executed by processing circuitry of system 2, may select a configuration of rules 196 based on etiological data for patient, e.g., any combination of one or more of the examples of sensed data 190, patient input 192, and EHR data 194 discussed above. In some examples, different sets of rules 196 tailored to different cohorts of patients may be available for selection for patient 4 based on such etiological data.

As discussed above, event assistant 176 may provide a conversational interface for patient 4 and/or bystander 26 to exchange information with computing device 12. Event assistant 176 may query the user regarding the condition of patient 4 in response to receiving the alert message from IMD 10. Responses from the user may be included as patient input 192. Event assistant 176 may use natural language processing and context data to interpret utterances by the user. In some examples, in addition to receiving responses to queries posed by the assistant, event assistant 176 may be configured to respond to queries posed by the user. In some examples, event assistant 176 may provide directions to and respond to queries regarding treatment of patient 4 from patient 4 or bystander 26.

Location service 178 may determine the location of computing device 12 and, thereby, the presumed location of patient 4. Location service 178 may use global position system (GPS) data, multilateration, and/or any other known techniques for locating computing devices.

Figure 4:
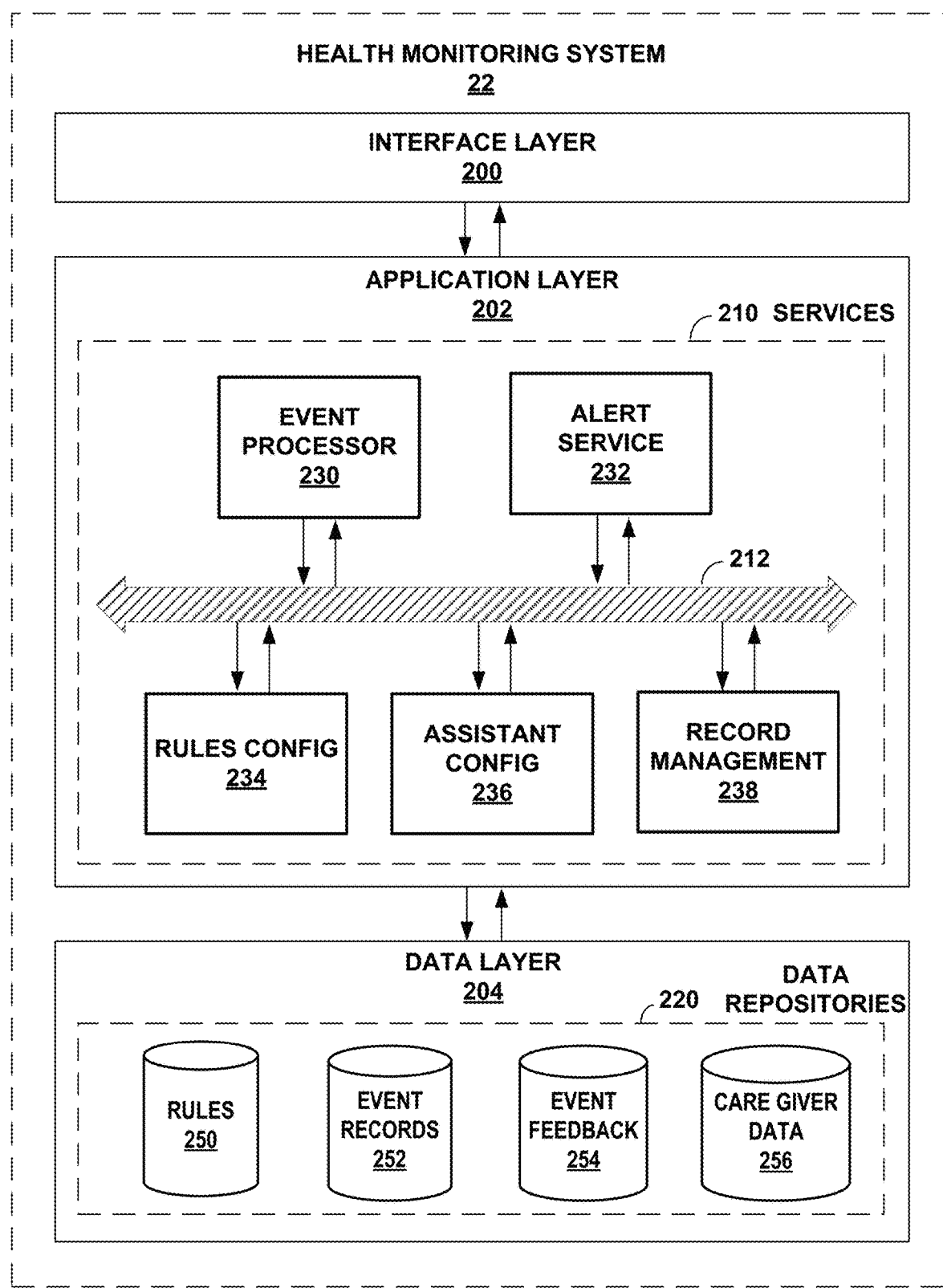
FIG. 4 is a block diagram illustrating an example configuration of a health monitoring system that operates in accordance with one or more techniques of the present disclosure.

FIG. 4 is a block diagram illustrating an operating perspective of HMS 22. HMS 22 may be implemented in a computing system 20, which may include hardware components such as those of computing device 12, e.g., processing circuitry, memory, and communication circuitry, embodied in one or more physical devices. FIG. 4 provides an operating perspective of HMS 22 when hosted as a cloud-based platform. In the example of FIG. 4, components of HMS 22 are arranged according to multiple logical layers that implement the techniques of this disclosure. Each layer may be implemented by one or more modules comprised of hardware, software, or a combination of hardware and software.

Computing devices, such as computing devices 12, IoT devices 30, computing devices 38, and computing device 42, operate as clients that communicate with HMS 22 via interface layer 200. The computing devices typically execute client software applications, such as desktop application, mobile application, and web applications. Interface layer 200 represents a set of application programming interfaces (API) or protocol interfaces presented and supported by HMS 22 for the client software applications. Interface layer 200 may be implemented with one or more web servers.

As shown in FIG. 4, HMS 22 also includes an application layer 202 that represents a collection of services 210 for implementing the functionality ascribed to HMS herein. Application layer 202 receives information from client applications, e.g., an alert of an acute health event from a computing device 12 or IoT device 30, and further processes the information according to one or more of the services 210 to respond to the information. Application layer 202 may be implemented as one or more discrete software services 210 executing on one or more application servers, e.g., physical or virtual machines. That is, the application servers provide runtime environments for execution of services 210. In some examples, the functionality interface layer 200 as described above and the functionality of application layer 202 may be implemented at the same server. Services 210 may communicate via a logical service bus 212. Service bus 212 generally represents a logical interconnections or set of interfaces that allows different services 210 to send messages to other services, such as by a publish/subscription communication model.

Data layer 204 of HMS 22 provides persistence for information in PPEMS 6 using one or more data repositories 220. A data repository 220, generally, may be any data structure or software that stores and/or manages data. Examples of data repositories 220 include but are not limited to relational databases, multi-dimensional databases, maps, and hash tables, to name only a few examples.

As shown in FIG. 4, each of services 230-238 is implemented in a modular form within HMS 22. Although shown as separate modules for each service, in some examples the functionality of two or more services may be combined into a single module or component. Each of services 230-238 may be implemented in software, hardware, or a combination of hardware and software. Moreover, services 230-238 may be implemented as standalone devices, separate virtual machines or containers, processes, threads or software instructions generally for execution on one or more physical processors.

Event processor service 230 may be responsive to receipt of an alert transmission from computing device(s) 12 and/or IoT device(s) 30 indicating that IMD 10 detected an acute health event of patient and, in some examples, that the transmitting device confirmed the detection. Event processor service 230 may initiate performance of any of the operations in response to detection of an acute health event ascribed herein to HMS 22, such as communicating with patient 4, bystander 26, and care providers 40, activating drone 46 and, in some cases, analyzing data to confirm or override the detection of the acute health event by IMD 10.

Record management service 238 may store the patient data included in a received alert message within event records 252. Alert service 232 may package the some or all of the data from the event record, in some cases with additional information as described herein, into one more alert messages for transmission to bystander 26 and/or care providers 40. Care giver data 256 may store data used by alert service 232 to identify to whom to send alerts based on locations of potential bystanders 26 and care givers 40 relative to a location of patient 4 and/or applicability of the care provided by care givers 40 to the acute health event experienced by patient 4.

In examples in which HMS 22 performs an analysis to confirm or override the detection of the acute health event by IMD 10, event processor service 230 may apply one or more rules 250 to the data received in the alert message, e.g., to feature vectors derived by event processor service 230 from the data. Rules 250 may include one or more models, algorithms, decision trees, and/or thresholds, which may be developed by rules configuration service 234 based on machine learning. Example machine learning techniques that may be employed to generate rules 250 can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, Convolution Neural Networks (CNN), Long Short Term Networks (LSTM), the Apriori algorithm, K-Means Clustering, k-Nearest Neighbour (kNN), Learning Vector Quantization (LVQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

In some examples, in addition to rules used by HMS 22 to confirm acute health event detection, (or in examples in which HMS 22 does not confirm event detection) rules 250 maintained by HMS 22 may include rules 196 utilized by computing devices 12 and rules 84 used by IMD 10. In such examples, rules configuration service 250 may be configured to develop and maintain rules 196 and rules 84. Rules configuration service 234 may be configured to develop different sets of rules 84, 196, 250, e.g., different machine learning models, for different cohorts of patients. Rules configuration service 234 may be configured to modify these rules based on event feedback data 254 that indicates whether the detections and confirmations of acute health events by IMD 10, computing device 12, and/or HMS 22 were accurate. Event feedback 254 may be received from patient 4, e.g., via computing device(s) 12, or from care providers 40 and/or EHR 24. In some examples, rules configuration service 234 may utilize event records from true and false detections (as indicated by event feedback data 254) and confirmations for supervised machine learning to further train models included as part of rules 250.

As illustrated in the example of FIG. 4, services 210 may also include an assistant configuration service 236 for configuring and interacting with event assistant 176 implemented in computing device 12 or other computing devices. For example, assistant configuration service 236 may provide event assistants updates to their natural language processing and context analyses to improve their operation over time. In some examples, assistant configuration service 236 may apply machine learning techniques to analyze sensed data and event assistant interactions stored in event records 252, as well as the ultimate disposition of the event, e.g., indicated by EHR 24, to modify the operation of event assistants, e.g., for patient 4, a class of patients, all patients, or for particular users or devices, e.g., care givers, bystanders, etc.

Figure 5:
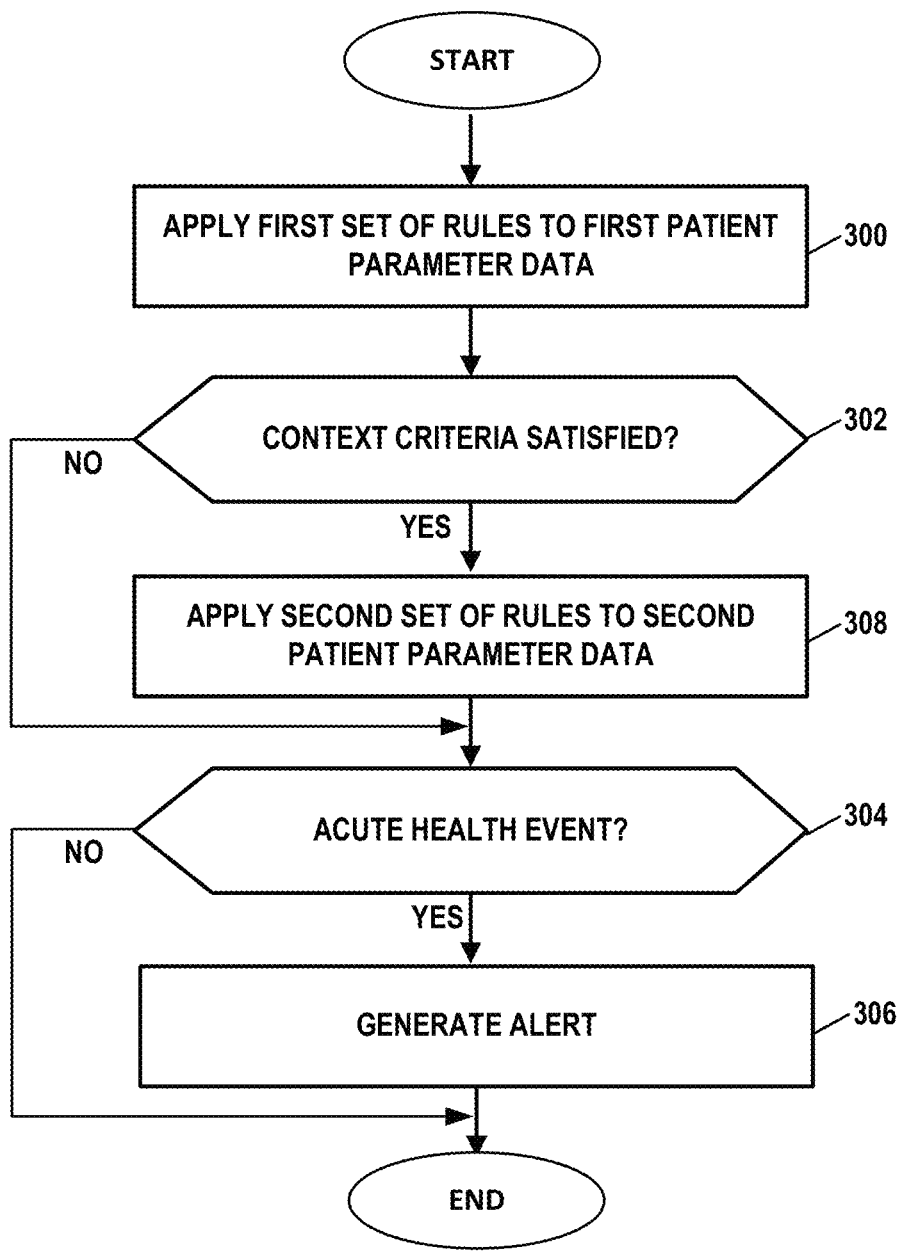
FIG. 5 is a flow diagram illustrating an example operation for applying rules to patient parameter data to determine whether an acute health event is detected.

FIG. 5 is a flow diagram illustrating an example operation for applying rules to patient parameter data to determine whether an acute health event is detected. The example operation of FIG. 5 may be performed by processing circuitry of any one of IMD 10, computing device(s) 12, 38, 42, IoT devices 30, AED 44, drone 46, or HMS 22 (e.g., by processing circuitry 50 or 130 implementing rules engine 74 or 172 and applying rules 84 or 196), or by processing circuitry of two or more of these devices respectively performing portions of the example operation.

According to the example of FIG. 5, the processing circuitry applies a first set of rules to first patient parameter data for a first determination of whether an acute health event, e.g., SCA, is detected (300). The processing circuitry determines whether one or more context criteria associated with the first determination are satisfied (302). If the one or more context criteria are not satisfied (NO of 302), the processing circuitry may determine whether the acute health event is detected based on the first determination (304). If the acute health event is detected (YES of 304), the processing circuitry may generate an alert, e.g., a message to another device and/or a user-perceptible alert as described herein (306). If the acute health event is not detected (NO of 304) or the alert has been generated, the example operation of FIG. 5 may end. If the one or more context criteria are satisfied (YES of 302), the processing circuitry may apply a second set of rules to second patient parameter data for a second determination of whether the acute health event, e.g., SCA, is detected (308), and determine whether the acute health event is detected based on the second determination (304).

The first and second sets of rules are different in at least one aspect. In some examples, the second set of rules comprises at least one machine learning model. In some examples, both the first and second sets of rules comprise at least one machine learning model.

In some examples, the processing circuitry determines a risk score of the acute health event, e.g., SCA, based on the application of the first set of rules to the first patient parameter data, and compares the risk score to a threshold to determine whether the one or more context criteria are satisfied. In some examples, the context indicating that the second set of rules should be applied to the second patient parameter data may be that the risk score produced by the first determination does not meet a threshold indicating a sufficient certainty that the acute health event is occurring. The risk score may be a percentage likelihood of the acute health event.

In some examples, the processing circuitry determines a confidence level of the first determination of whether the acute health event is detected, and compares the confidence level to a threshold. In some examples, the one or more context criteria may be satisfied where the first determination does not have a threshold degree of confidence, or where the first determination is associated with a likelihood of being a false positive that exceeds a threshold. In such examples, application of the second set of rules to the second patient parameter data may act as a "tie-breaker" when the first determination is not confident. In some examples, the processing circuitry determines that the one or more context criteria are satisfied when input from a user, e.g., the patient, contradicts the first determination (e.g., that the acute health event was detected or not detected), indicating that the likelihood that the first determination is false may be relatively high.

The processing circuitry may determine a confidence level of the first determination of whether the acute health event is present using a variety of techniques. For example, the application of the first set of rules to the first patient parameter data may produce a level of confidence through its output, e.g., a risk score. In such examples, a higher output indicating a higher likelihood of the acute health event may indicate a higher level of confidence. Examples of rules that may produce such outputs include machine learning models and time-domain signal processing algorithms.

In some examples, the processing circuitry may determine a noise level of one or more signals from which the first patient parameter data is determined. In such examples, the processing circuitry may determine a confidence level of the first determination of whether the acute health event is present based on a noise level. In general, confidence level and noise level may be inversely related. In some examples, the processing circuitry may determine the confidence level based on health record data for patient 4. For example, if a clinician has indicated in a health record or via programming IMD 10 that patient 4 has experienced a myocardial infarction or has heart failure, confidence levels may be increased and/or thresholds included in the rules applied to the first patient parameter data may be lowered.

In some examples, a context criterion may be satisfied when a component of system 2, e.g., IMD 10 or computing devices 12, has sufficient power to enable the application of the second set of rules to the second patient parameter data. In some examples, to determine whether the one or more context criteria are satisfied, the processing may determine a power level of system 2, e.g., of the relevant device, and compare the power level threshold. In some examples, the second patient parameter data includes data of at least one patient parameter that is not included in the first patient parameter data. In some examples, the processing circuitry activates a sensor to sense this patient parameter, e.g., when the device including the sensor has sufficient power for the measurement.

In some examples, the first patient parameter data and the second patient parameter data are both sensed by an implantable medical device. In some examples, the at least one patient parameter that is included in the second patient parameter data but not included in the first patient parameter data is sensed by an external device. In some examples, processing circuitry 50 of IMD 10 or processing circuitry 130 of computing device(s) 12 (or IoT devices 30 or the other devices discussed herein) performs each of sub-operations 300-308. In other examples, processing circuitry 50 of IMD 10 performs the first determination of whether the acute health event, e.g., SCA, is detected (300), and processing circuitry 130 of computing device(s) 12 (or IoT devices 30 or the other devices discussed herein) performs each of sub-operations 302-308.

In some examples, the first patient parameter data includes at least one patient parameter determined from ECG data, and the at least one patient parameter comprises a patient parameter determined from at least one of heart sounds of the patient, an impedance of the patient, motion of the patient, respiration of the patient, posture of the patient, blood pressure of the patient, a chemical detected in the patient, or an optical signal from the patient. In some examples, the first patient parameter data and second patient parameter data may be determined using different combinations of sensors, e.g., internal and/or external sensors. The first and second determinations may be considered different tiers, with the second determination utilizing additional sensor(s), data, and/or power if the context suggests it would be desirable to supplement the first determination.

In some examples, the processing circuitry selects at least one of the second set of rules or the parameters used for the second patient parameter data based on at least one of user (e.g., patient or care giver or bystander) input or medical record information of the patient. In some examples, the user input and/or medical history information may include information entered by a clinician when programming IMD 10. For example, the processing circuitry may select at least one of the second set of rules or the parameters used for the second patient parameter data based on user input or medical record information indicating a particular symptom or condition of the patient. In some examples, the first patient parameter data comprises data for a first set of patient parameters, and the processing circuitry may select at least one of the second set of rules or a second patient parameter for the second patient parameter data based on the level. A level for a particular parameter that is clinically significant but contrary to the first determination (either a detection or non-detection), may suggest that the second determination should be performed, and should be performed with a particular parallel (but different) or orthogonal patient parameter to resolve the uncertainty about whether the acute health event is detected.

In some examples, the first patient parameter data includes at least one patient parameter determined from ECG data of the patient, and the second patient parameter data comprises at least one of a morphological change or a frequency shift of the ECG data over time. The processing circuitry may analyze ECG data for timing or morphology changes. For example, morphological or frequency changes as a ventricular fibrillation persists may indicate an increase lethality of the ventricular fibrillation. In some examples, the rules applied processing circuitry may determine a higher likelihood of the acute health event, e.g., lethal ventricular fibrillation or SCA, the presence of such morphological or frequency shifts.

The example operation of FIG. 5 may result in a hierarchy of rules or even sensor measurements. In some examples, one or more sensors may be activated in certain contexts, and may be inactive for first determinations of whether the acute health event is detected, e.g., to conserve power of IMD 10. For example, if in a first determination ECG data indicates ventricular fibrillation and other sensor data indicates no pulse and no heart sounds, there may be no need for the second determination. But if those levels of evidence is not high, e.g., not sure if it definitely ventricular fibrillation there might be faint heart sounds or faint pulses, then a second determination could be employed.

Further, the rules and sensors used in either or both of the first as second determinations can be configured/personalized for each patient based on their medical history from EMR or their history of previous events or by their physicians/caregivers depending on the situation. For example, if a caregiver has to leave town for few days, the processing circuitry could configure the rules to be satisfied by lower levels of evidence, e.g., automatically, which may advantageously tailor the monitoring provided by system 2 to the context of patient 4 and care givers of the patient.

Figure 6:
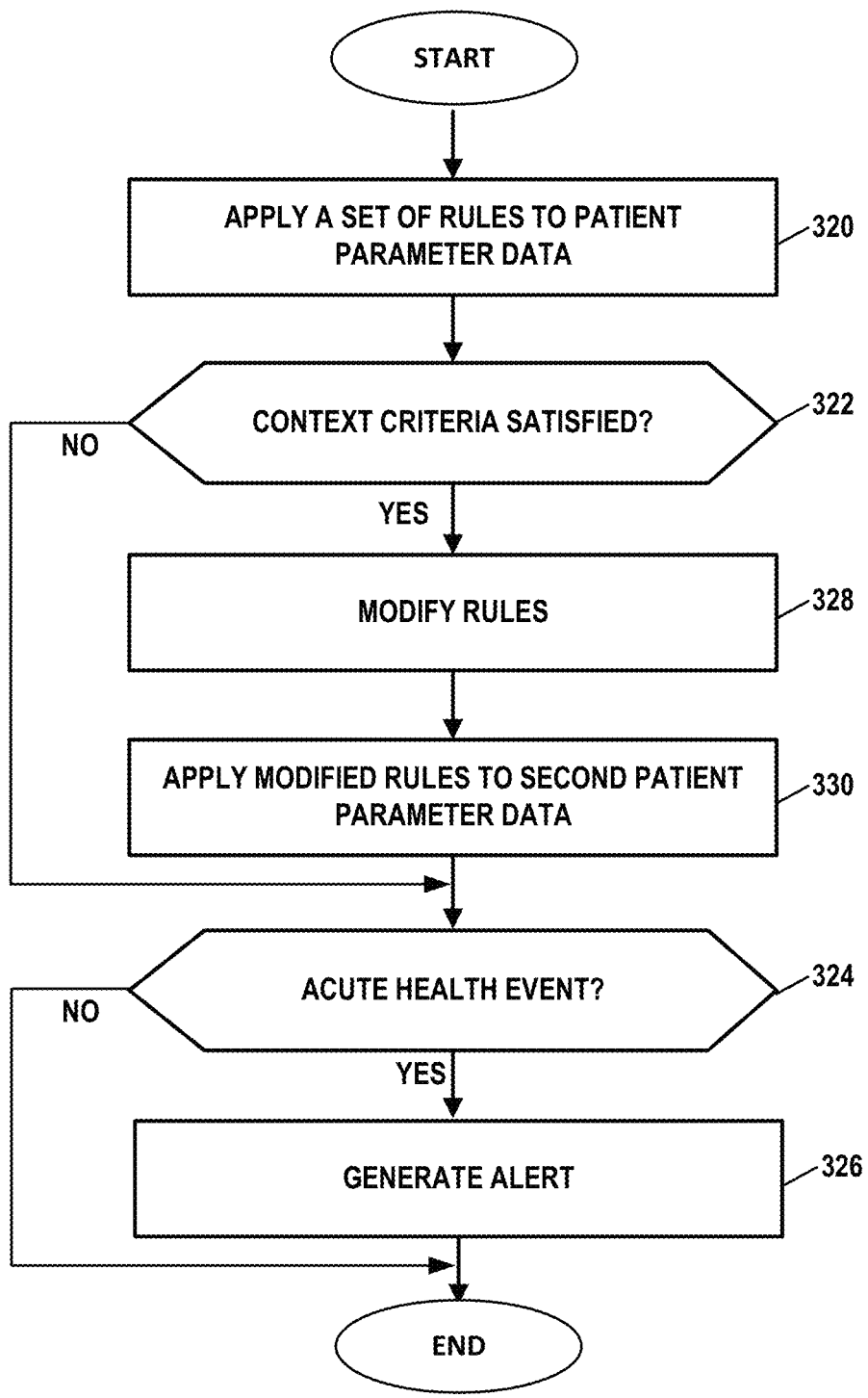
FIG. 6 is a flow diagram illustrating another example operation for applying rules to patient parameter data to determine whether an acute health event is detected.

FIG. 6 is a flow diagram illustrating another example operation for applying rules to patient parameter data to determine whether an acute health event is detected. The example operation of FIG. 6 may be performed by processing circuitry of any one of IMD 10, computing device(s) 12, 38, 42, IoT devices 30, AED 44, drone 46, or HMS 22 (e.g., by processing circuitry 50 or 130 implementing rules engine 74 or 172 and applying rules 84 or 196), or by processing circuitry of two or more of these devices respectively performing portions of the example operation.

According to the example of FIG. 6, the processing circuitry applies a set of rules to patient parameter data to determine whether an acute health event, e.g., SCA, is detected (320). The processing circuitry determines whether one or more context criteria associated with the determination are satisfied (322). If the one or more context criteria are not satisfied (NO of 322), the processing circuitry may determine whether the acute health event is detected based on the determination (324). If the acute health event is detected (YES of 324), the processing circuitry may generate an alert, e.g., a message to another device and/or a user-perceptible alert as described herein (326). If the acute health event is not detected (NO of 324) or the alert has been generated, the example operation of FIG. 6 may end. If the one or more context criteria are satisfied (YES of 322), the processing circuitry may apply modify the set of rules (328), apply second patient parameter data to the second set of rules (330), and determine whether the acute health event is detected based on the application of the second patient parameter data to the second set of rules (324).

The processing circuitry may determine whether the one or more context criteria are satisfied in the manner described with respect to FIG. 5. In some examples, the first and second patient parameter data may be determined using the same patient parameters or (with respect to at least one parameter) different patient parameters. In some examples, the first patient parameter data and the second patient parameter data include at least one common patient parameter, and the processing circuitry may change a mode sensing for the common patient parameter between the first patient parameter data and the second patient parameter data in response to satisfaction of the one or more context criteria. For example, the processing circuitry may change a sampling frequency for the common patient parameter.

In some examples in which IMD 10 senses patient parameters used to determine the first patient parameter data, the processing circuitry may determine that a context criterion is satisfied by detecting that IMD 10 has flipped or otherwise migrated within patient 4. Such migration may lead to significant changes in patient parameter data, e.g., ECG data, impedance data, or heart sound data. Changing a mode employed by IMD 10 to sense one or more patient parameters, or changing rules to account for changes in patient parameter data resulting from device migration, may help ameliorate the device migration and maintain effective acute health event detection. In addition to the mode of sensing and/or rules, the processing circuitry may adjust other aspects of system, such mode of wireless communication between the IMD and other devices. Techniques for detecting and mitigating migration of IMD 10 are described in commonly-assigned U.S. patent application Ser. No. 17/101,945, filed Nov. 23, 2020 by Anderson et al., titled "DETECTION AND MITIGATION OF INACCURATE SENSING BY AN IMPLANTED SENSOR OF A MEDICAL SYSTEM," which is incorporated herein by reference in its entirety.

In some examples, the processing circuitry determines that the one or more context criteria are satisfied when the processing circuitry determines that the acute health event, e.g., ventricular tachyarrhythmia or SCA, is detected, but the patient or another user cancels the alarm or otherwise provides user input contradicting the determination. In such examples, the processing circuitry may modify one or both of the sensed patient parameters or the rules applied to the patient parameter data.

For example, the patient may have tolerated a rapid ventricular tachycardia that lasted for a sustained period (e.g., a programmed 10 or 20 seconds), but could experience another arrhythmia, e.g., syncope, soon even though the patient believes they are OK. The modification may include adapting the rules based on the rhythm. Sometimes a long duration episode accelerates to ventricular fibrillation or more rapid ventricular tachycardia. Sometimes ventricular fibrillation slows down. In either case, the modification could include changing a heart rate threshold, e.g., applying hysteresis to the heart rate threshold. In some examples, ventricular fibrillation becomes ugly/fine and is very difficult to sense. In such examples, the modification may include changing a ventricular depolarization detection threshold to allow more undersensing of depolarizations.

In some examples, the processing circuitry determines that the one or more context criteria are satisfied based on a recent history of high arrhythmia burden. Some patients have electrical storms. Their electrolytes may be imbalanced, and they may experience a cluster of ventricular arrhythmias, but the patient parameter data may not satisfy the rules for detection of the acute health event. In such cases, the processing circuitry may adapt a tachyarrhythmia duration the threshold, may alert patient and caregivers and inform them to seek care ASAP, and/or may alert a clinician and send patient parameter data, e.g., ECG data, so the clinician can review.

Figure 7:
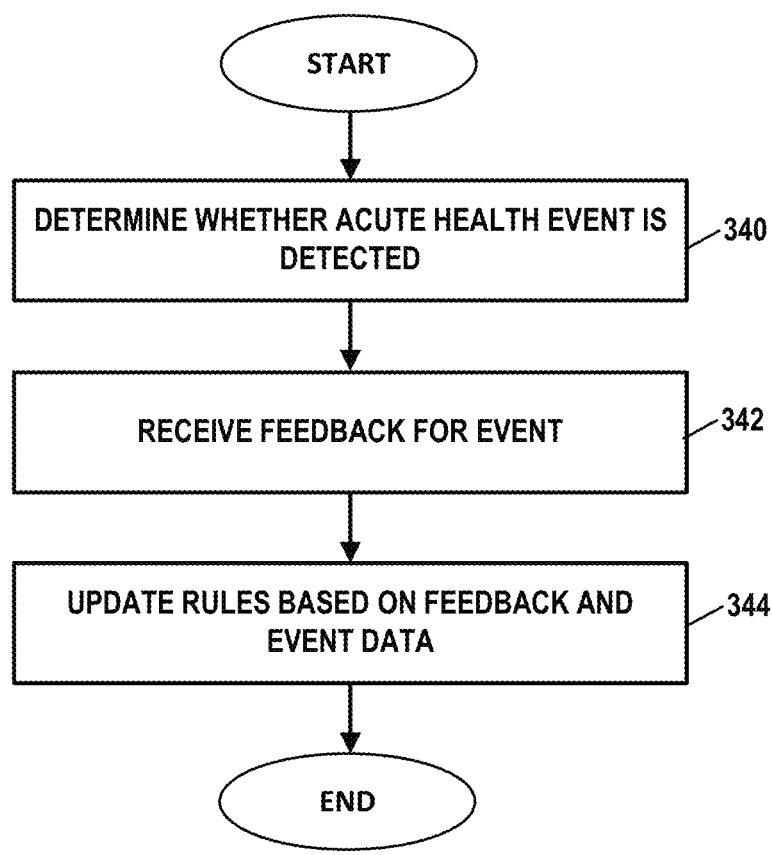
FIG. 7 is a flow diagram illustrating an example operation for configuring rules applied to patient parameter data to determine whether an acute health event is detected for a patient.

FIG. 7 is a flow diagram illustrating an example operation for configuring rules applied to patient parameter data to determine whether an acute health event is detected for a patient. The example operation of FIG. 7 may be performed by processing circuitry that implements HMS 22, e.g., that implements rules configuration service 234. In some examples, the operation of FIG. 7 may be performed by processing circuitry of any one of IMD 10, computing device(s) 12, 38, 42, IoT devices 30, AED 44, drone 46, or HMS 22, e.g., implementing a rules configuration module, or by processing circuitry of two or more of these devices respectively performing portions of the example operation.

According to the example operation of FIG. 7, the processing circuitry determines whether an acute health event, e.g., SCA, is detected (340). The processing circuitry receives feedback for the event (342). The feedback indicates whether the detection a true or false positive, or the non-detection is a true or false negative. The processing circuitry may receive the feedback from patient 4, care giver 40, bystander 26, or EHR 24. The processing circuitry updates rules (e.g., rules 84, rules 196, and/or rules 250) based on the feedback and event data, e.g., event data 86 or event records 252. In some examples, uses the event data as a training set for one or more machine learning models based on the feedback.

Through predictive and "self-learning" techniques, the operation of a system used to provide an alert for SCA can be improved. Time-to-treatment (either CPR or a shock from AED 44) may be improved by providing a timely alert, either to bystanders 26 or the EMS care givers 40. The information used to improve the performance could include physiologic sensor data that may indicate an SCA event is likely (QT prolongation, T-wave alternans, changes in respiration rate or thoracic impedance, etc.). The information used to improve the performance could include information indicating whether the prior SCA event was alerted appropriately and accurately, clinical or physiologic characteristics of the patient (disease state, weight, gender, etc.), data from EHR 24, and data input from the patient (e.g., symptom logging, confirmation that he/she is OK and not suffering from SCA, etc.).

Implementing the example operation of FIG. 7, the processing circuitry may personalize the rules for patient 4 over time. If patient 4 has a lot of false positives, the example operation of FIG. 7 may modify the rules to be less sensitive and, conversely, if the patient 4 has a lot of false negatives may modify the rules to be more sensitive. In some examples, the processing circuitry may use the feedback and event data to update rules, e.g., machine learning models, for other patients, such as all patients whose IMDs are served by EMS 22, or a particular population or cohort of patients. In some examples, the processing circuitry may use data from a number of sources (e.g., computing devices 12, IoT devices 30, AED 44, or drone 46) to modify the rules or the collection of patient parameter data. Data used by processing circuitry to update rules may include data indicating a duration of CPR, e.g., input by a user, or data collected using an accelerometer, speaker, light detector, or camera on a computing device or IoT device.

Figure 8:
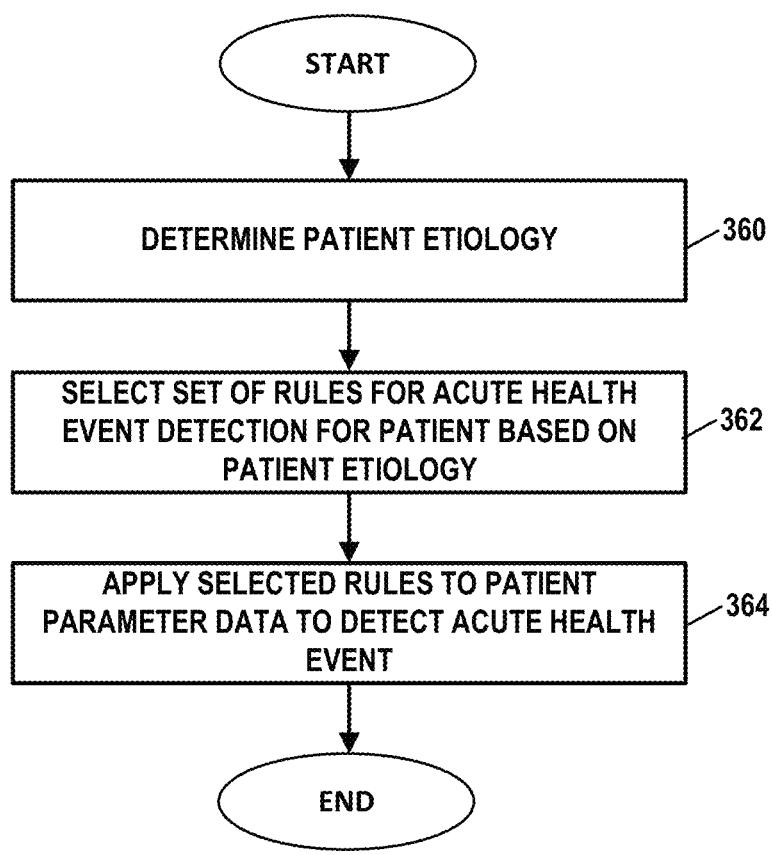
FIG. 8 is a flow diagram illustrating another example operation for configuring rules applied to patient parameter data to determine whether an acute health event is detected for a patient.

FIG. 8 is a flow diagram illustrating another example operation for configuring rules applied to patient parameter data to determine whether an acute health event is detected for a patient. The example operation of FIG. 7 may be performed by processing circuitry that implements HMS 22, e.g., that implements rules configuration service 234. In some examples, the operation of FIG. 8 may be performed by processing circuitry of any one of IMD 10, computing device(s) 12, 38, 42, IoT devices 30, AED 44, drone 46, or HMS 22, e.g., implementing a rules configuration module, or by processing circuitry of two or more of these devices respectively performing portions of the example operation.

According to the example operation of FIG. 8, the processing circuitry determines an etiology or risk stratification of patient 4 (360). The processing circuitry selects a set of rules (e.g., a set of rules 84, rules 196, and/or rules 250), which may be a first set of rules and/or a second set of rules, for acute health event, e.g., SCA, detection for patient 4 based on the patient etiology (362). In some examples, rules 250 include different sets of rules for different patient cohorts having different etiologies, and processing circuitry may select different rule sets to implement as rules 84 in IMD 10 and rules 196 in computing device(s) 12 for a given patient based on the etiology of that patient. The processing circuitry may apply the selected set of rules to patient parameter data to determine whether the acute health event is detected using any of the techniques described herein (364).

Detection of SCA can be achieved by looking at a number of possible markers that occur prior to and during the event.

The best markers to detect an impending or ongoing event are likely to be different based an etiology of the patient. An SCA detection algorithm which uses a generic algorithm designed for a broad population may not achieve satisfactory sensitivity and specificity. The etiology of patient 4 may include baseline characteristics, medical history, or disease state. The etiology of patient 4 may include any EHR data 194 described herein, as well as patient activity level or metabolite level. With such possible inputs, the rules could look for certain markers to exhibit certain trends or threshold crossings to detect an impending or ongoing acute health event, e.g., SCA.

In some examples, selection of a set of rules may include modification of a universal rule set to turn certain rules (or markers of the acute health event) on or off, or change the weight of certain rules or markers. In some examples, a family of devices could be designed such that individual models have sensors or calculation for only a limited set of inputs motivated by a need to reduce manufacturing costs or energy consumption.

While SCA is typically detected by heart rate/rhythm, rules related to other patient parameter data may be set to a heightened alert based patient etiology. For example, a patient with prior myocardial infarction may have rules that weigh ischemia factors such as ST segment elevation more heavily than for patients lacking this etiology. As another example, a patient with long QT syndrome may have rules that more heavily weight QT interval and activity. As another example, rules for a heart failure patient may have rules that apply greater weight to patient parameter data related to lung fluid and QRS duration.

In some examples, processing circuitry of system 2 may use patient etiology to "personalize" other aspects of the operation of system 2 for patient 4 or a cohort including patient 4. For example, the processing circuitry may provide alerts and user interfaces that guide care givers 40, bystanders 26, patient 4, or others based on the etiology. The processing circuitry can provide patient-specific care recommendations (e.g., AED or potential drug therapy for prevention or therapy of SCA). The ability of the system to detect the acute health event with adequate sensitivity and specificity may, for example, guide an EMS care giver 40 to what they can expect when they arrive on the scene and how best to treat the presenting rhythm, e.g., is the patient hypoxic, hypovolemic, hypothermic, tension pneumothorax, cardiac tamponade (the H's and T's of Advanced Cardiac Life Support). The etiology may indicate of patient 4 is more at risk for pulseless electrical activity vs. ventricular fibrillation/ventricular tachycardia. The processing circuitry of system 2 may provide care givers information based on the etiology current patient parameter data of patient 4, such as recommendations to provide CPR or defibrillation, provide drugs, or induce hypothermia. The processing circuitry of system 2 may recommend patient-specific care actions based on the etiology, e.g. purchase an AED or Chest Compression System (LUCAS).

Although described primarily in the context of detection of SCA, system 2 may be used to detection any of a number of acute health events of patient 4. For example, system 2 may be used to detect stroke. Stroke can often present in the form of facial droop. This change in facial tone could be identified using facial image processing on a computing device 12, e.g., a smartphone, or IoT 30. Such image processing could be a primary indicator of possible stroke or a part of a confirmation after another device indications changes related to stroke.

Some computing devices 12, e.g. smartphones, include facial processing for access, e.g., faceID, and are accessed in this manner frequently throughout the day. Processing circuitry, e.g., of the computing device, may analyze the facial images to detect subtle changes in facial tone over time. The processing circuitry could detect possible stroke, and various devices of system 2 could provide alerts as described herein.

In some examples, in response to detection based on the camera images, the device could output a series of prompts (audible and/or visual) to access a current state of patient 4. Patient 4 could be prompted to repeat a phrase or answer audible questions to assess cognitive ability. The device could use additional motion processing to further verify the state of patient 4, e.g., using an accelerometer of computing device 12A and/or 12B. Changes in body motion and asymmetry, e.g., of the face and/or body motion, are indicative of stroke. In some examples, the device may ask patient 4 questions. Processing circuitry may analyze the response to detect speech difficulties associated with stroke. In some examples, the alert could include information on where the facial tone has changed, which could aid in diagnosis by guiding care givers 40 to possible primary locations for scans (ex: left side droop=right side clot).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module, unit, or circuit for purposes of clarity, it should be understood that the techniques of this disclosure may be performed by a combination of units, modules, or circuitry associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processing circuitry" as used herein may refer to any of the foregoing structure or any other physical structure suitable for implementation of the described techniques. Also, the techniques could be fully implemented in one or more circuits or logic elements.

The following examples are illustrative of the techniques described herein.

Example 1. A system comprising processing circuitry and memory. The memory comprises program instructions that, when executed by the processing circuitry, cause the processing circuitry to: apply a first set of rules to first patient parameter data for a first determination of whether sudden cardiac arrest of a patient is detected; determine that one or more context criteria of the first determination are satisfied; and in response to satisfaction of the one or more context criteria, apply a second set of rules to second patient parameter data for a second determination of whether sudden cardiac arrest of the patient is detected. At least the second set of rules comprises a machine learning model, and the second patient parameter data comprises at least one patient parameter that is not included in the first patient parameter data.

Example 2. The system of example 1, wherein the machine learning model comprises a first machine learning model and the first set of rules comprises a second machine learning model.

Example 3. The system of example 1 or 2, wherein first patient parameters of the first patient parameter data are sensed by an implantable medical device, and the at least one patient parameter is sensed by an external device.

Example 4. The system of any of examples 1 to 3, wherein the first patient parameter data includes at least one patient parameter determined from electrocardiogram data of the patient, and the at least one parameter comprises a patient parameter determined from at least one of heart sounds of the patient, an impedance of the patient, motion of the patient, respiration of the patient, posture of the patient, blood pressure of the patient, a chemical detected in the patient, or an optical signal from the patient.

Example 5. The system of any of examples 1 to 4, wherein the instructions cause the processing circuitry to activate a sensor to sense the at least one patient parameter in response to satisfaction of the one or more context criteria.

Example 6. The system of any of examples 1 to 5, wherein the instructions cause the processing circuitry to: determine a risk score of sudden cardiac arrest based on the application of the first set of rules to the first patient parameter data, and wherein, to determine that the one or more context criteria are satisfied, the instructions cause the processing circuitry to compare the risk score to a threshold.

Example 7. The system of any of examples 1 to 6, wherein, to determine that the one or more context criteria are satisfied, the instructions cause the processing circuitry to: determine a confidence level of the first determination of whether sudden cardiac arrest of the patient is detected; and compare the confidence level to a threshold.

Example 8. The system of any of examples 1 to 7, wherein, to determine that the one or more context criteria are satisfied, the instructions cause the processing circuitry to: determine a power level of the system; and compare the power level of the system to a threshold.

Example 9. The system of any of examples 1 to 8, wherein the instructions cause the processing circuitry to select at least one of the second set of rules or the second patient parameter data based on at least one of user input associated with the first determination, medical record information of the patient, or a duration of the sudden cardiac arrest indicated by the first determination.

Example 10. The system of any of examples 1 to 9, wherein the first patient parameter data comprises a first set of patient parameters, and wherein the instructions cause the processing circuitry to: determine a level of at least one of the first set of patient parameters in the first patient parameter data; and select at least one of the second set of rules or a second patient parameter of the second patient parameter data based on the level.

Example 11. The system of any of examples 1 to 10, wherein the first patient parameter data includes at least one patient parameter determined from electrocardiogram data of the patient, and the second patient parameter data comprises at least one of a morphological change or a frequency shift of the electrocardiogram data over time.

Example 12. The system of any of examples 1 to 11, wherein the first patient parameter data and the second patient parameter data include at least one common patient parameter, wherein the instructions cause the processing circuitry to change a mode sensing the common patient parameter between the first patient parameter data and the second patient parameter data in response to satisfaction of the one or more context criteria.

Example 13. The system of any of examples 1 to 12, wherein the processing circuitry comprises processing circuitry of at least one of an implantable medical device or a computing device configured for wireless communication with the implantable medical device.

Example 14. The system of any of examples 1 to 13, wherein the instructions cause the processing circuitry to select at least one of the first set of rules or the second set of rules based on health record data of the patient.

Example 15. The system of any of examples 1 to 14, wherein the instructions cause the processing circuitry to update at least one of the first set of rules or the second set of rules based on feedback data indicative of whether the second determination was true or false.

Example 16. A method comprising, by processing circuitry: applying a first set of rules to first patient parameter data for a first determination of whether sudden cardiac arrest of a patient is detected; determining that one or more context criteria of the first determination are satisfied; and in response to satisfaction of the one or more context criteria, applying a second set of rules to second patient parameter data for a second determination of whether sudden cardiac arrest of the patient is detected. At least the second set of rules comprises a machine learning model, and the second patient parameter data comprises at least one patient parameter that is not included in the first patient parameter data.

Example 17. The method of example 16, wherein the machine learning model comprises a first machine learning model and the first set of rules comprises a second machine learning model.

Example 18. The method of example 16 or 17, wherein first patient parameters of the first patient parameter data are sensed by an implantable medical device, and the at least one patient parameter is sensed by an external device.

Example 19. The method of any of examples 16 to 18, wherein the first patient parameter data includes at least one patient parameter determined from electrocardiogram data of the patient, and the at least one parameter comprises a patient parameter determined from at least one of heart sounds of the patient, an impedance of the patient, motion of the patient, respiration of the patient, posture of the patient, blood pressure of the patient, a chemical detected in the patient, or an optical signal from the patient.

Example 20. The method of any of examples 16 to 19, further comprising activating a sensor to sense the at least one patient parameter in response to satisfaction of the one or more context criteria.

Example 21. The method of any of examples 16 to 20, further comprising determining a risk score of sudden cardiac arrest based on the application of the first set of rules to the first patient parameter data, wherein determining that the one or more context criteria are satisfied comprises comparing the risk score to a threshold.

Example 22. The method of any of examples 16 to 21, wherein determining that the one or more context criteria are satisfied comprises: determining a confidence level of the first determination of whether sudden cardiac arrest of the patient is detected; and comparing the confidence level to a threshold.

Example 23. The method of any of examples 16 to 22, wherein determining that the one or more context criteria are satisfied comprises: determining a power level of the system; and comparing the power level of the system to a threshold.

Example 24. The method of any of examples 16 to 23, further comprising selecting at least one of the second set of rules or the second patient parameter data based on at least one of user input associated with the first determination or medical record information of the patient.

Example 25. The method of any of examples 16 to 24, wherein the first patient parameter data comprises a first set of patient parameters, and the method further comprises: determining a level of at least one of the first set of patient parameters; and selecting at least one of the second set of rules or the second patient parameter data based on the level.

Example 26. The method of any of examples 16 to 25, wherein the first patient parameter data includes at least one patient parameter determined from electrocardiogram data of the patient, and the second patient parameter data comprises at least one of a morphological change or a frequency shift of the electrocardiogram data over time.

Example 27. The method of any of examples 16 to 26, wherein the first patient parameter data and the second patient parameter data include at least one common patient parameter, and the method further comprises changing a mode sensing the common patient parameter between the first patient parameter data and the second patient parameter data in response to satisfaction of the one or more context criteria.

Example 28. The method of any of examples 16 to 27, further comprising select at least one of the first set of rules or the second set of rules based on health record data of the patient.

Example 29. The method of any of examples 16 to 28, further comprising updating at least one of the first set of rules or the second set of rules based on feedback data indicative of whether the second determination was true or false.

Example 30. A non-transitory computer-readable storage medium comprising instructions that, when executed by processing circuitry, cause the processing circuitry to perform the method of any of examples 16 to 29.

Various examples have been described. These and other examples are within the scope of the following claims.

What is claimed is:

1. A system comprising:
an insertable cardiac monitor configured for insertion into a patient;
processing circuitry; and
memory comprising program instructions that, when executed by the processing circuitry, cause the processing circuitry to:
apply a set of rules to first patient parameter data sensed by the insertable cardiac monitor for a first determination that sudden cardiac arrest of the patient is occurring or has occurred;
determine a confidence level of the first determination that sudden cardiac arrest of the patient is occurring or has occurred;
determine that one or more context criteria of the first determination are satisfied based at least in part on the determined confidence level being below a threshold;
change a mode of sensing a common patient parameter between the first patient parameter data and second patient parameter data in response to satisfaction of the one or more context criteria;
activate another device to sense at least one patient parameter that is not included in the first patient parameter data in response to satisfaction of the one or more context criteria, the another device being other than the insertable cardiac monitor, and the another device being in physical proximity and external to the patient; and
apply a machine learning model to the second patient parameter data for a second determination that sudden cardiac arrest of the patient is occurring or has occurred in response to the satisfaction of the one or more context criteria,
wherein the first patient parameter data and the second patient parameter data each include the common patient parameter, and the second patient parameter data further comprises the at least one patient parameter that is not included in the first patient parameter data.

2. The system of claim 1, wherein the machine learning model comprises a first machine learning model and the set of rules comprises a second machine learning model.

3. The system of claim 1, wherein the first patient parameter data includes at least one patient parameter determined from electrocardiogram data of the patient, and the at least one parameter that is not included in the first patient parameter data comprises a patient parameter determined from at least one of heart sounds of the patient, an impedance of the patient, motion of the patient, respiration of the patient, posture of the patient, blood pressure of the patient, a chemical detected in the patient, or an optical signal from the patient.

4. The system of claim 1, wherein the instructions cause the processing circuitry to select at least one of the machine learning model or the second patient parameter data based on at least one of user input associated with the first determination, medical record information of the patient, or a duration of the sudden cardiac arrest indicated by the first determination.

5. The system of claim 1, wherein the first patient parameter data comprises a first set of patient parameters, and wherein the instructions cause the processing circuitry to:
determine a level of at least one of the first set of patient parameters in the first patient parameter data; and
select at least one of machine learning model or a second patient parameter of the second patient parameter data based on the level.

6. The system of claim 1, wherein the first patient parameter data includes at least one patient parameter determined from electrocardiogram data of the patient, and the second patient parameter data comprises at least one of a morphological change or a frequency shift of the electrocardiogram data over time.

7. The system of claim 1, wherein the processing circuitry comprises processing circuitry of at least one of an implantable medical device or a computing device configured for wireless communication with the implantable medical device.

8. The system of claim 1, wherein the instructions cause the processing circuitry to select the machine learning model based on health record data of the patient.

9. The system of claim 1, wherein the instructions cause the processing circuitry to update at least one of the set of rules or the machine learning model based on feedback data indicative of whether the second determination was true or false.

10. The system of claim 1, wherein the set of rules does not include a machine learning model.

11. The system of claim 1, wherein the instructions cause the processing circuitry to only apply the machine learning model to the second patient parameter data in response to the satisfaction of the one or more context criteria.

12. The system of claim 1, wherein the processing circuitry comprises:
    processing circuitry of the insertable cardiac monitor configured to apply the set of rules to the first patient parameter data for the first determination that sudden cardiac arrest of the patient is occurring or has occurred; and
    processing circuitry of the another device configured to apply the machine learning model to the second patient parameter data for the second determination that sudden cardiac arrest of the patient is occurring or has occurred.

13. The system of claim 1, wherein the instructions cause the processing circuitry to cause the another device to output an indication of sudden cardiac arrest in response to the second determination that sudden cardiac arrest of the patient is occurring or has occurred indicating sudden cardiac arrest.

14. A method comprising, by processing circuitry:
    applying a set of rules to first patient parameter data sensed by an insertable cardiac monitor implanted in a patient for a first determination that sudden cardiac arrest of the patient is occurring or has occurred;
    determining a confidence level of the first determination that sudden cardiac arrest of the patient is occurring or has occurred;
    determining that one or more context criteria of the first determination are satisfied based at least in part on the determined confidence level being below a threshold;
    changing a mode of sensing a common patient parameter between the first patient parameter data and second patient parameter data in response to satisfaction of the one or more context criteria;
    activating another device to sense and collect at least one patient parameter that is not included in the first patient parameter data in response to satisfaction of the one or more context criteria, the another device being other than the insertable cardiac monitor, and the another device being in physical proximity and external to the patient; and
    applying a machine learning model to the second patient parameter data for a second determination that sudden cardiac arrest of the patient is occurring or has occurred in response to satisfaction of the one or more context criteria,
    wherein the first patient parameter data and the second patient parameter data each include the common patient parameter, and the second patient parameter data further comprises at least one patient parameter that is not included in the first patient parameter data.

15. The method of claim 14, wherein the machine learning model comprises a first machine learning model and the set of rules comprises a second machine learning model.

16. The method of claim 14, wherein the first patient parameter data includes at least one patient parameter determined from electrocardiogram data of the patient, and the at least one parameter that is not included in the first patient parameter data comprises a patient parameter determined from at least one of heart sounds of the patient, an impedance of the patient, motion of the patient, respiration of the patient, posture of the patient, blood pressure of the patient, a chemical detected in the patient, or an optical signal from the patient.

17. The method of claim 14, further comprising selecting at least one of the machine learning model or the second patient parameter data based on at least one of user input associated with the first determination or medical record information of the patient.

18. The method of claim 14, wherein the first patient parameter data comprises a first set of patient parameters, and the method further comprises:
    determining a level of at least one of the first set of patient parameters; and
    selecting at least one of the machine learning model or the second patient parameter data based on the level.

19. The method of claim 14, wherein the first patient parameter data includes at least one patient parameter determined from electrocardiogram data of the patient, and the second patient parameter data comprises at least one of a morphological change or a frequency shift of the electrocardiogram data over time.

20. The method of claim 14, further comprising selecting the machine learning model based on health record data of the patient.

21. The method of claim 14, further comprising updating at least one of the set of rules or the machine learning model based on feedback data indicative of whether the second determination was true or false.

22. The method of claim 14, further comprising causing the another device to output an indication of sudden cardiac arrest in response to the second determination of that sudden cardiac arrest of the patient is occurring or has occurred indicating sudden cardiac arrest.

23. A non-transitory computer-readable storage medium comprising instructions that, when executed by processing circuitry, cause the processing circuitry to:
    apply a set of rules to first patient parameter data sensed by an insertable cardiac monitor implanted in a patient for a first determination that sudden cardiac arrest of the patient is detected;
    determine a confidence level of the first determination that sudden cardiac arrest of the patient is occurring or has occurred;
    determine that a one or more context criteria of the first determination are satisfied based at least in part on the determined confidence level being below a threshold;
    change a mode of sensing a common patient parameter between the first patient parameter data and second patient parameter data in response to satisfaction of the one or more context criteria;
    activate another device to sense and collect at least one patient parameter that is not included in the first patient parameter data in response to satisfaction of the context criteria, the another device being other than the insertable cardiac monitor, and the another device being in physical proximity and external to the patient; and
    apply a machine learning model to the second patient parameter data for a second determination that sudden cardiac arrest of the patient is occurring or has occurred in response to satisfaction of the one or more context criteria, wherein the first patient parameter data and the second patient parameter data include the common patient parameter, and the second patient parameter data further comprises at least one patient parameter that is not included in the first patient parameter data.

\* \* \* \* \*